US008507231B2

(12) United States Patent
Abbas et al.

(10) Patent No.: US 8,507,231 B2
(45) Date of Patent: Aug. 13, 2013

(54) HIGH THROUGHPUT SCREENING PLATFORM FOR HIGH ETHANOL PRODUCTION

(75) Inventors: Jason Abbas, Perry, IA (US); George Aux, Durham, NC (US); Joe Byrum, West Des Moines, IA (US); My Nguyen, Ankeny, IA (US); Kirk Noel, Granger, IA (US); Mark P Seymour, Bracknell (GB)

(73) Assignee: Syngenta Participations AG, Basel (CH)

( * ) Notice: Subject to any disclaimer, the term of this patent is extended or adjusted under 35 U.S.C. 154(b) by 565 days.

(21) Appl. No.: 12/626,232

(22) Filed: Nov. 25, 2009

(65) Prior Publication Data
US 2010/0151440 A1 Jun. 17, 2010

Related U.S. Application Data

(60) Provisional application No. 61/200,189, filed on Nov. 25, 2008, provisional application No. 61/200,225, filed on Nov. 25, 2008.

(51) Int. Cl.
| | |
|---|---|
| C12P 7/06 | (2006.01) |
| C12P 7/08 | (2006.01) |
| C12P 7/10 | (2006.01) |
| C12Q 1/34 | (2006.01) |
| C12Q 1/40 | (2006.01) |
| C12Q 1/54 | (2006.01) |

(52) U.S. Cl.
USPC ............... 435/161; 435/4; 435/14; 435/18

(58) Field of Classification Search
USPC ..................... 435/4, 14, 18, 161
See application file for complete search history.

(56) References Cited

U.S. PATENT DOCUMENTS

| | | | | |
|---|---|---|---|---|
| 2002/0192701 | A1* | 12/2002 | Adey | 435/6 |
| 2010/0151440 | A1* | 6/2010 | Abbas et al. | 435/4 |

OTHER PUBLICATIONS

Lovitt et al. Ethanol Production by Thermophilic Bacteria: Biochemical Basis for Ethanol and Hydrogen Tolerance in Clostridium thermohydrosulfuricum. Journal of Bacteriology (Jun. 1988) vol. 170, No. 6, pp. 2809-2815.*
Comberbach, et al. 1983. Automatic on-line fermentation headspace gas analysis using a computer-controlled gas chromatograph. Biotechnology and Bioengineering, vol. 25, Issue 11, pp. 2503-2518.*
Cordenunsi et al., 1985. Mathematical model for the alcoholic fermentation in batch culture: Comparison between complete and incomplete factorial (33) designs. Journal of Biotechnology, vol. 2, pp. 1-120 1-12.*
Linko et al.,1993. A Critical Study of Lignin Peroxidase Activity Assay by Veratryl Alcohol Oxidation. Biotechnology Techniques vol. 7, No. 1, pp. 75-80.*
Davis. 2001. Corn Milling, Processing and Generation of Co-products. Minnesota Nutrition Conference Minnesota Corn Growers Association Technical Symposium. Sep. 11, 2001, pp. 1-7.*
Smith. 2008. Brewing an Irish Stout Beer Recipe. Beer Smith Home Brewing Blog, Mar. 14, 2008, pp. 1-3.*
Singh et al.1996. Wet Milling of Corn-A Review of Laboratory-Scale and Pilot Plant-Scale Procedures. Cereal Chemistry, vol. 73, No. 6, pp. 659-667.*
Han et al. 1987. Amylolysis of Raw Corn by *Aspergillus niger* for Simultaneous Ethanol Fermentation. Biotechnology and Bioengineering, vol. 30, pp. 225-232.*

\* cited by examiner

*Primary Examiner* — Jon P Weber
*Assistant Examiner* — Kailash C Srivastava
(74) *Attorney, Agent, or Firm* — Dana Rewoldt

(57) ABSTRACT

Provided herein are high throughput methods for converting starch-containing plant material to ethanol, wherein the conversion process is performed at a small scale. This high-throughput screening platform permits the evaluation of the ethanol obtained from starch-containing plant material in a rapid and efficient manner. The methods include obtaining a plurality of samples of starch-containing plant material and drying the samples to achieve a desired moisture level. The dried samples are liquefied under conditions sufficient to hydrolyze the starch-containing plant material to soluble dextrinized substrates. The liquefied samples are fermented in small volume headspace vials for a period of less than about 96 hours, and fermentation is terminated by pasteurization. Ethanol production is evaluated using headspace gas chromatography.

16 Claims, 10 Drawing Sheets

US 8,507,231 B2

HIGH THROUGHPUT SCREENING PLATFORM FOR HIGH ETHANOL PRODUCTION

REFERENCE TO RELATED APPLICATION

Figure 1:
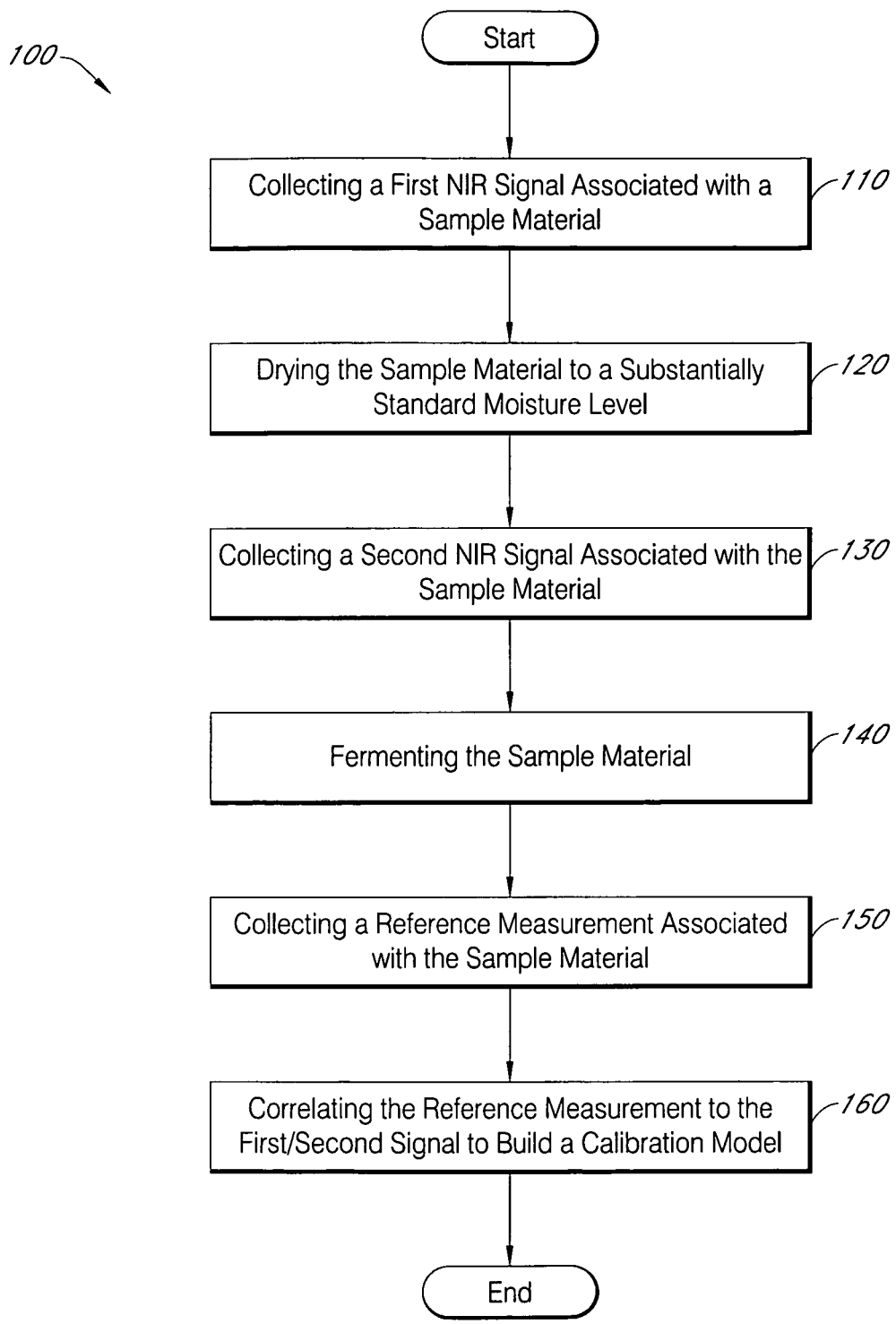

This application claims the benefit of priority two U.S. Provisional Application Ser. Nos. 61/200,225 and 61/200,189 filed on Nov. 25, 2008.

FIELD OF THE INVENTION

This invention relates to high-throughput methods for identifying optimal compositions and conditions for ethanol production.

BACKGROUND OF THE INVENTION

Ethanol fermentation is a biological process in which organic material is converted by microorganisms to simpler compounds, such as sugars. These fermentable compounds are then fermented by microorganisms to produce ethanol and $CO_2$. Ethanol has widespread application, including, as an industrial chemical, gasoline additive or straight liquid fuel. As a fuel or fuel additive, ethanol dramatically reduces air emissions while improving engine performance. As a renewable fuel, ethanol reduces national dependence on finite and largely foreign fossil fuel sources, while decreasing the net accumulation of carbon dioxide in the atmosphere.

Typically ethanol is produced by liquefying starch-containing material followed by sequential or simultaneous saccharification and fermentation. Liquefaction involves gelatinization of starch simultaneously with or followed by addition of alpha-amylase in order to degrade starch into dextrins. When producing ethanol the liquefied starch-containing material is saccharified. Saccharification is a step in which dextrins are converted to low molecular DP1-3 sugars that, e.g., can be converted by a yeast into ethanol.

The amount of ethanol produced from plant material can depend on the amount and availability of starch in the plant material, milling conditions, the type of yeast used, the fermentation conditions, and the like. Generally, plant varieties for use in ethanol production are selected based on the fermentability of the variety. In this field, although ethanol production has been greatly improved by new technologies, there are still challenges that need further investigations.

SUMMARY OF THE INVENTION

Provided herein are high throughput methods for converting starch-containing plant material to ethanol, wherein the conversion process is performed at a small scale. This high-throughput screening platform permits the evaluation of the ethanol obtained from starch-containing plant material in a rapid and efficient manner.

In its broad embodiment, the platform is an autosampling system which dries the samples, limits the dried samples exposure to atmospheric moisture, ferments the samples and captures headspace gas in an autosampling system for evaluation.

The methods comprise obtaining a plurality of samples of starch-containing plant material and drying the samples to achieve a desired moisture level. The moisture level can be achieved using a drying cabinet set at a relative humidity and temperature suitable for achieving the desired moisture level in the samples. In various embodiments, the desired moisture level is a terminal moisture level.

The dried samples are liquefied under conditions sufficient to hydrolyze the starch-containing plant material to soluble dextrinized substrates. The liquefaction steps are performed in a convected oven to maintain uniform temperature across all samples in the screening platform. The liquefied samples are fermented in small volume headspace vials for a period of less than about 96 hours, and fermentation is terminated by pasteurization. Ethanol production is evaluated using headspace gas chromatography.

The high throughput screening platform disclosed herein is suitable for rapid evaluation of various parameters of the starch-to-ethanol conversion process. One or more of these parameters can be modeled to achieve a desired fermentation product or to improve the efficiency of the starch-to-ethanol conversion process. Further, such a high throughput screening platform may be used to build a calibration model to calibrate for a testing device configured to quickly and non-destructively evaluate a sample biological material for ethanol yield.

The following embodiments are encompassed by the present invention. A high throughput platform for converting starch-containing plant material to one or more fermentation products. This platform comprises steps of: providing samples comprising starch-containing plant material, drying the samples to a specific moisture; fermenting each sample; evaluating the sample fermentation product. In one an embodiment of this invention, the samples are dried to a terminal moisture level.

In other embodiments of this invention, the sample fermentation product often is ethanol which can be evaluated using headspace gas chromatography. In its broad embodiment, the platform is an autosampling system which dries the samples, limits the dried samples exposure to atmospheric moisture, ferments the samples and captures headspace gas for evaluation. The high throughput nature of the invention is through the automated systems including the automatic system for headspace sampling.

This high throughput system of the present invention permits the small scale modeling of changes in the processes employed in a full sized ethanol plant. The consequences of changes in the processes or the inputs into these processes are captured within this high through put platform. Without directly mimicking the full scale of the processes within the specific ethanol plant, the present platform can incorporate the change with predictive results concerning the effect of the change in process and inputs within a specific plant. In some instance, the platform also comprises a liquefying step comprises heating the samples in a convected oven. The conversion of cellulosic or starch containing plant material into ethanol is impacted by efficiencies or inefficiencies of the liquefying and fermentation steps. With the present high throughput platform the liquefying step can be modeled for evaluation of the effects of pH, length of time or temperature, or some combination. This liquefying step can comprise addition of one or more starch-degrading enzymes, including alpha amylase. Starch degrading enzyme additions, or deletions are often modeled in the liquefying step. This platform provides a quick efficient model for evaluating the source of starch-degrading enzyme, the type of starch-degrading enzyme, the specific combination of starch-degrading enzymes, or any combinations.

The platform of the present invention can utilize starch-containing plant material which is processed by milling, crushing, rolling, or breaking up such plant material. The platform can model various sources of starch-containing plant material when these samples are dried. This method can further comprise a step of weighing an amount of each of the dried samples for the liquefying step, wherein said sample is maintained a climate-controlled relative humidity sufficient to maintain the specific moisture level of said samples.

BRIEF DESCRIPTION OF THE SEVERAL VIEWS OF THE DRAWING(S)

Having thus described the invention in general terms, reference will now be made to the accompanying drawing, and wherein:

FIG. 1 is a flow chart of a method according to one embodiment of the present invention including the steps of collecting a first signal associated with a sample material, drying the sample material to a substantially standard moisture level, collecting a second signal associated with a sample material, fermenting the sample material, collecting a reference measurement associated with the sample material, and correlating the reference measurement to at least one of the first and second signals.

Figure 2:
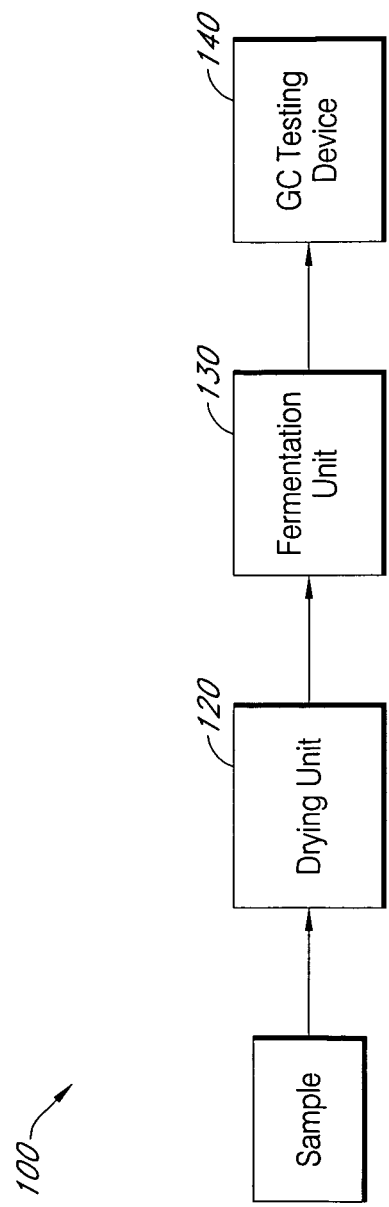

FIG. 2 is a schematic representation of a system used in a testing device configured to screen for ethanol production yield of an ethanol-producing material, according to one embodiment of the present invention.

Figure 3A:
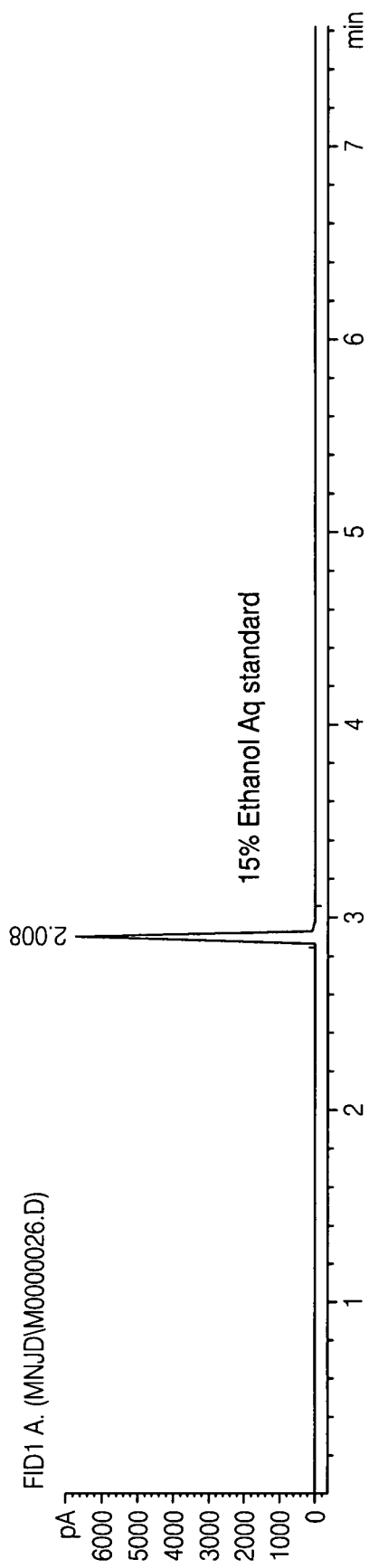
Figure 3B:
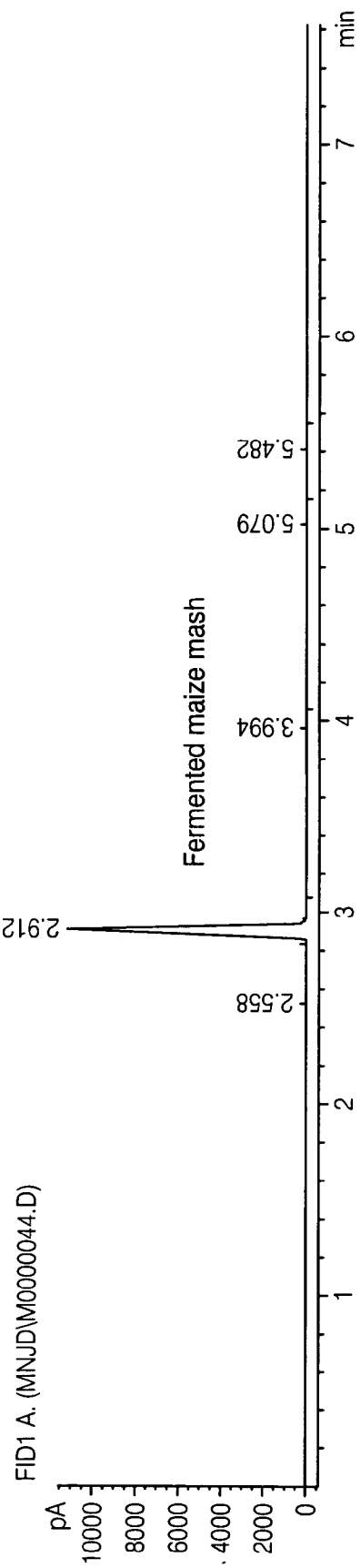
Figure 3C:
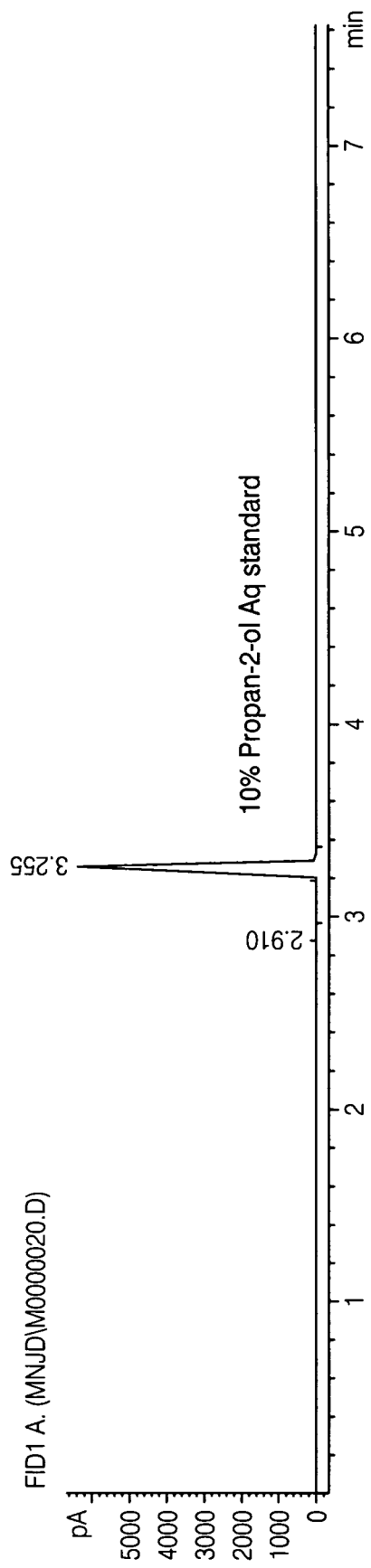
Figure 4A:
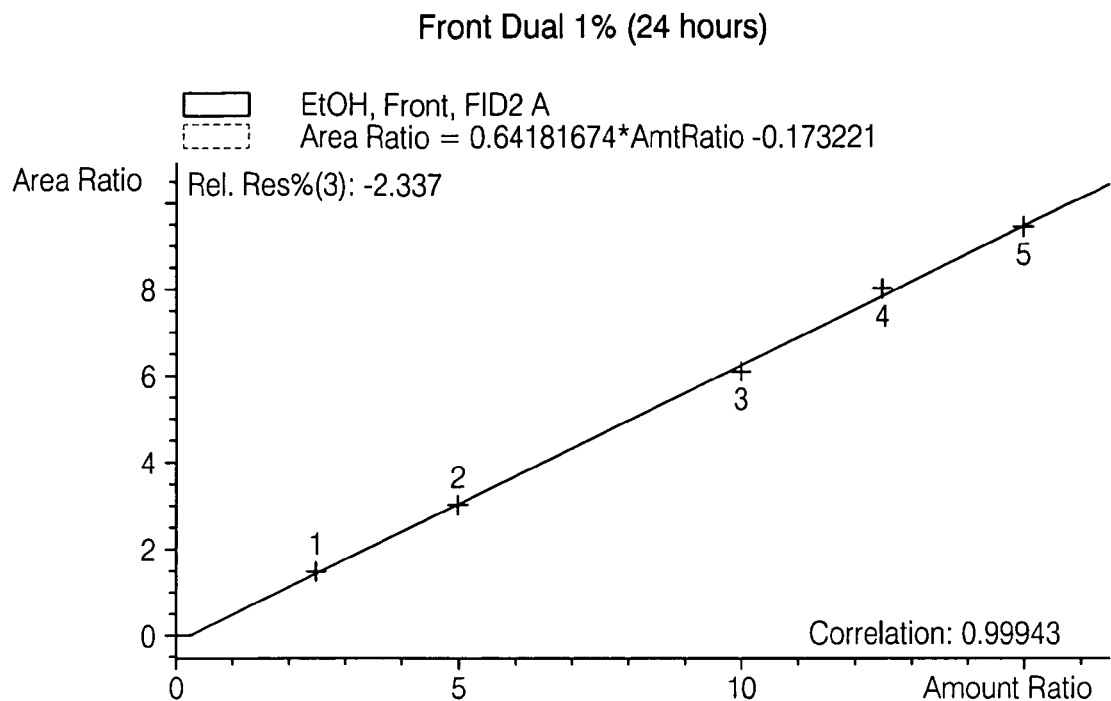
Figure 4B:
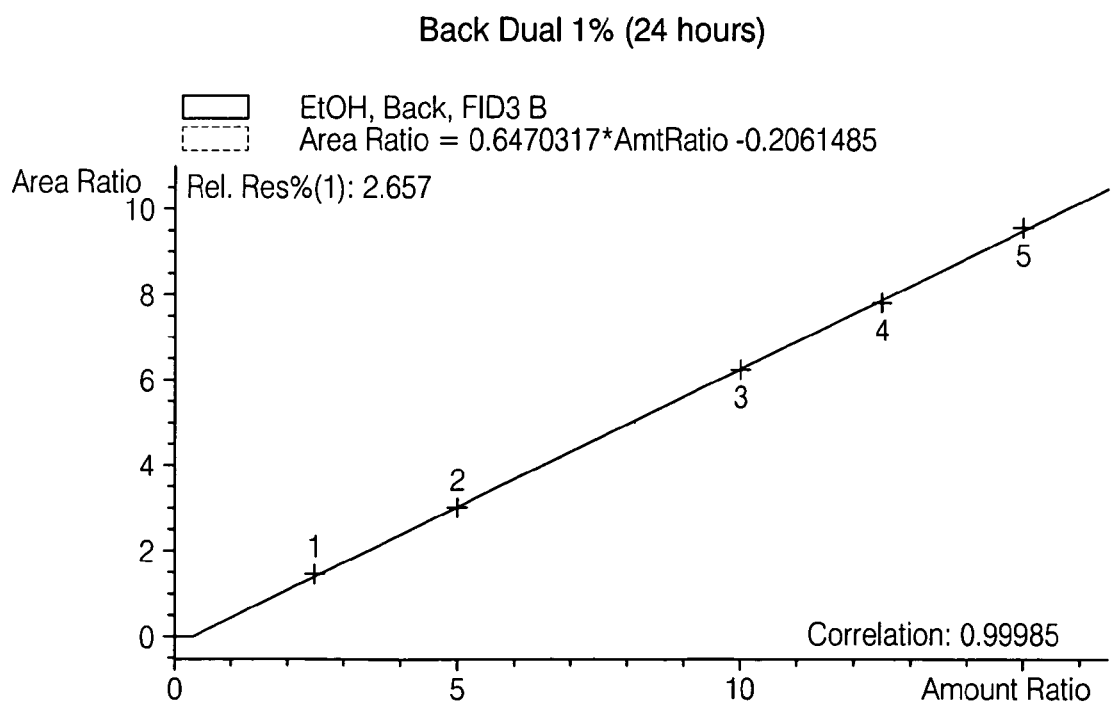
Figure 4C:
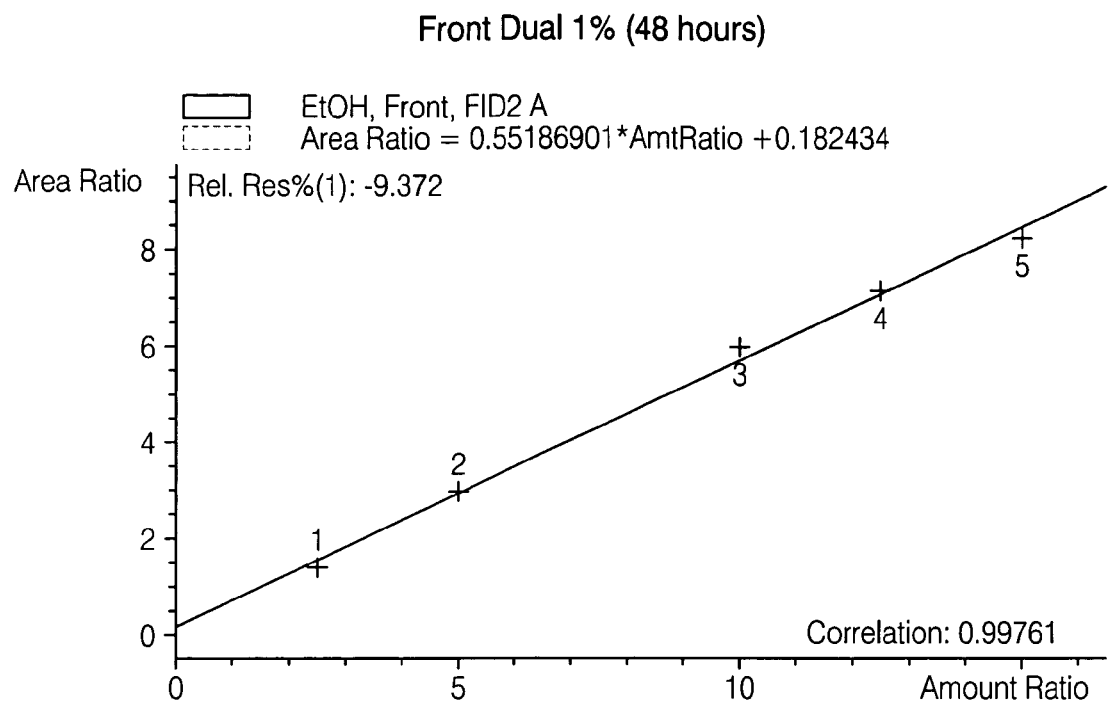
Figure 4D:
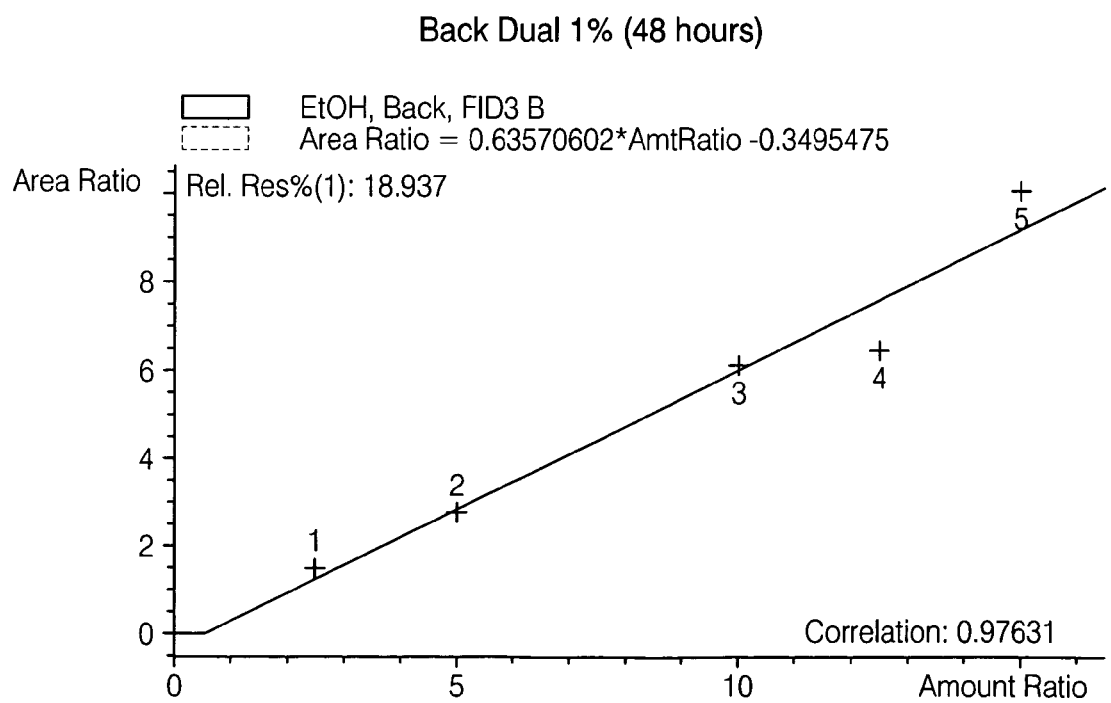
Figure 4E:
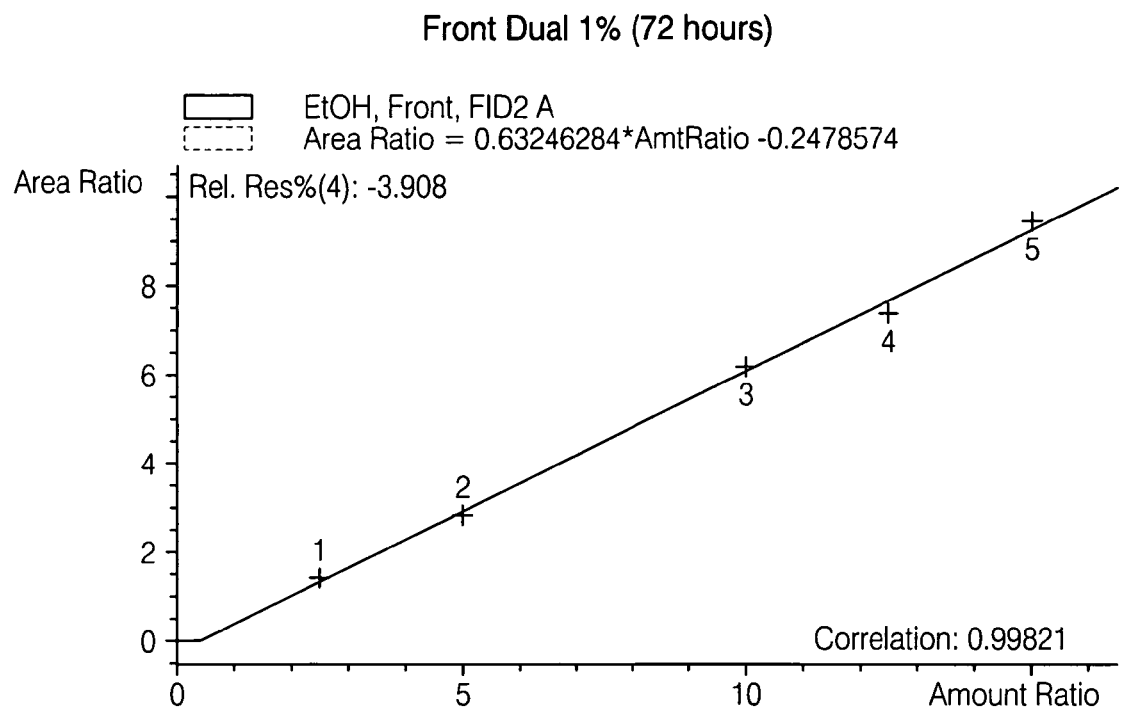
Figure 4F:
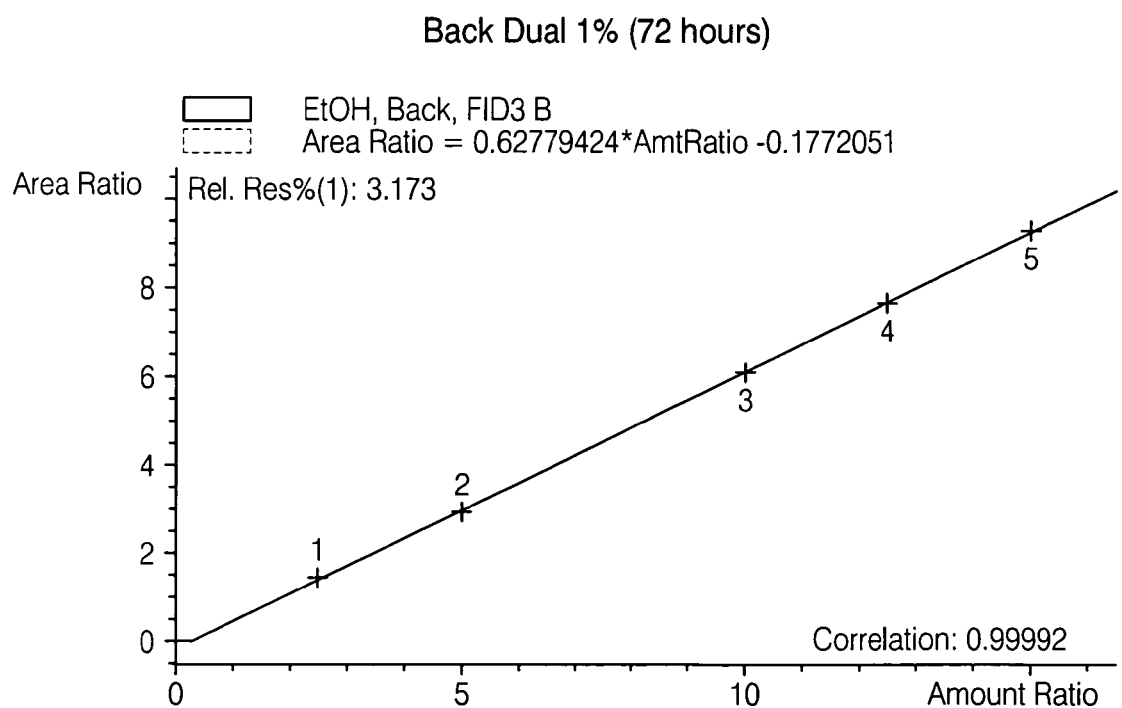
Figure 4G:
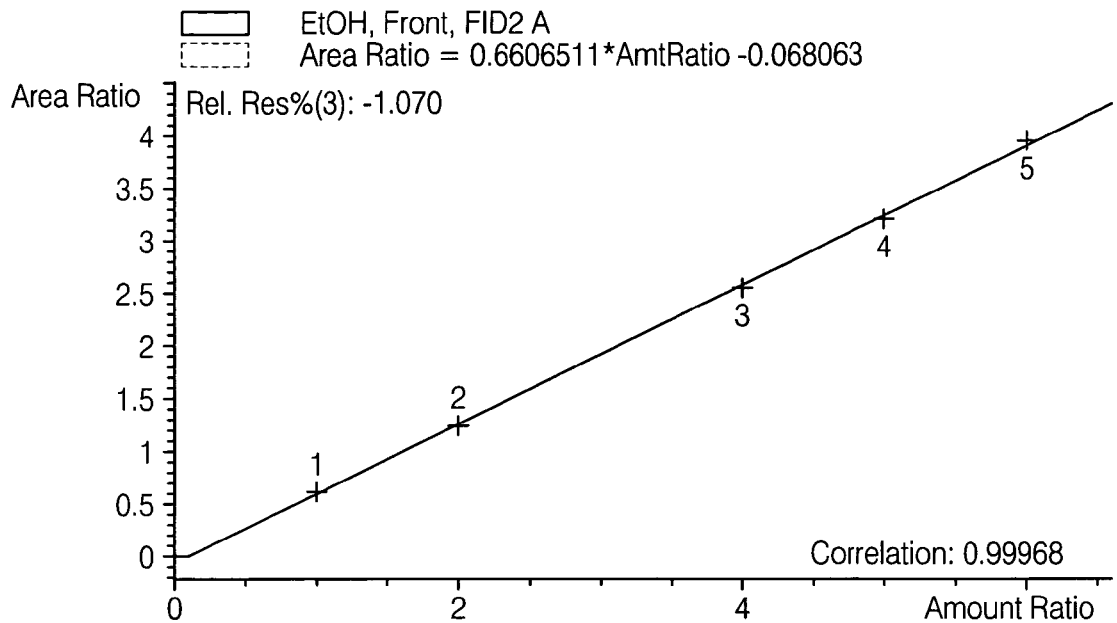
Figure 4H:
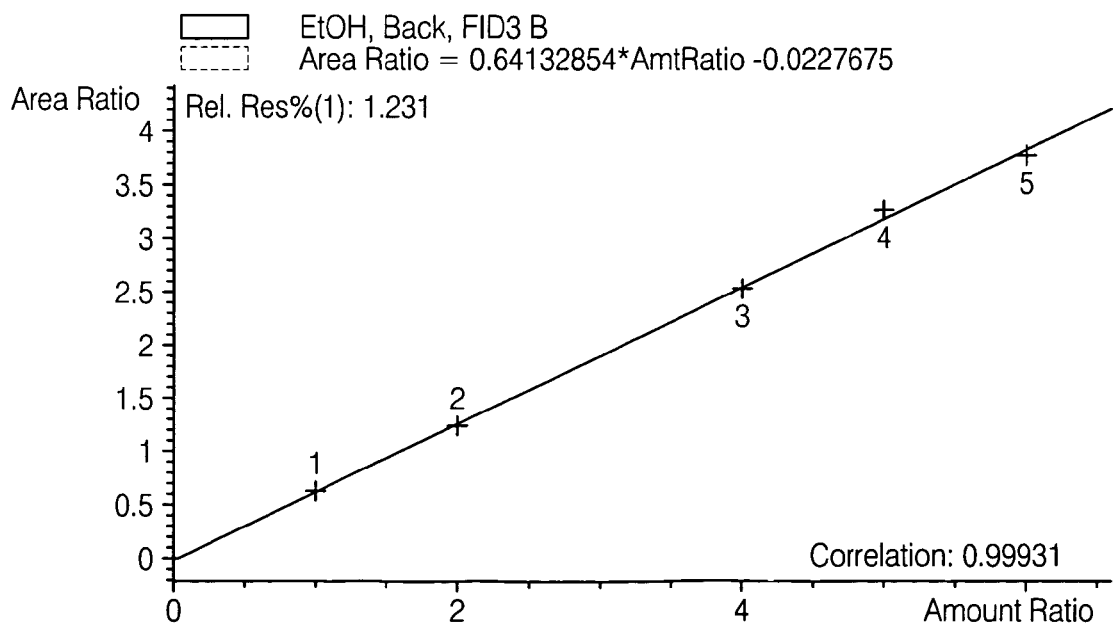

FIG. 3 is 3 sample chromatograms 15% Ethanol Standard, Fermented Maize and 10% Isopropanol Standard from experiment 3.

FIG. 4a-h are the calibration curves for the 1% front and back dual at 24, 48 and 72 hours respectively and the 2.5% front and back dual at 24 hours.

Figure 5:
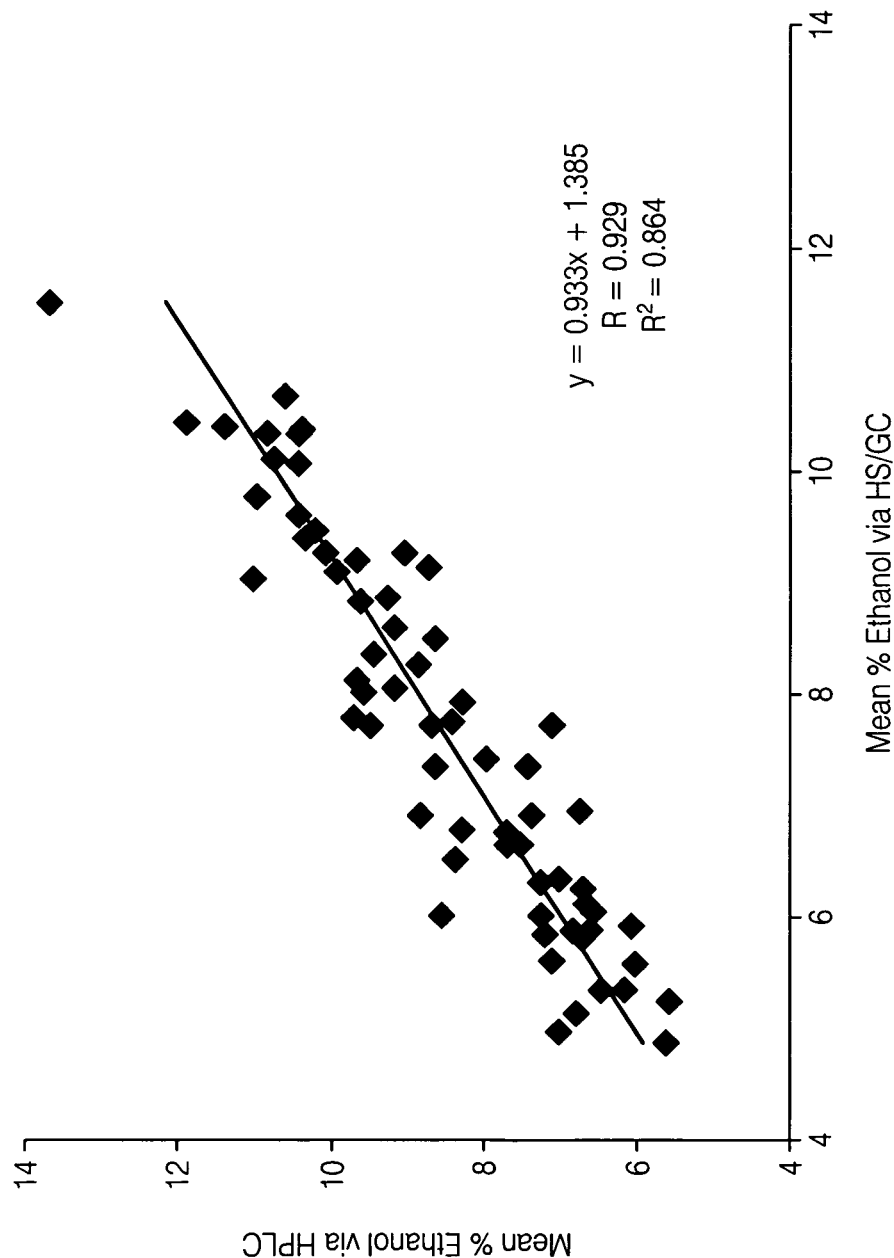

FIG. 5 illustrates the plotted data and fitted regression line of the Plot of Mean % Ethanol via HS/GC vs. Mean % Ethanol via HPLC from Experiment 5.

DETAILED DESCRIPTION OF THE INVENTION

Definitions for Calculations

The present disclosure now will be described more fully hereinafter with reference to the accompanying drawing in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Overview

In view of the increasing importance of ethanol fuels, improved processes for the hydrolysis of plant starch to fermentable sugars is highly desirable. For example, any improvement in the process that reduces time, expense, or energy expenditure or increases the quality of the resulting ethanol or another by-product of the ethanol production process is of interest.

The presently disclosed subject matter relates to a method and apparatus for testing different components of the starch/ethanol production system. The High Throughput Screening Platform permits the evaluation of the ethanol obtained from starch-containing plant material in a rapid and efficient manner. The screening platform comprises an ethanol production process performed in a small-scale manner to allow screening of multiple samples simultaneously. Such a platform provides a significant advantage over full-scale conventional ethanol production processes in that multiple reactions can be performed in a significantly reduced amount of time. Further, such a platform may readily and efficiently provide a calibration model for a testing device used to evaluate ethanol yields.

For the purposes of the present invention, a "conventional ethanol production process" comprises liquefaction of at least about 25 grams of processed plant material (e.g., ground samples) in the presence of one or more starch-degrading enzymes, fermentation of the resulting mash in a fermentation vessel for at least about 72 hours, and measurement of ethanol production using high-performance liquid chromatography. In various embodiments, the number of ethanol conversion reactions that can be performed using the methods disclosed herein is at least about 5 times, or at least about 10 times, the number of reactions that can be performed in the same amount of time and space as conventional ethanol conversion processes.

The methods disclosed herein, such as, for example, method 100 (FIG. 1), facilitate modeling of different parameters of the ethanol production process, including, but not limited to, input material and liquefaction, saccharification, and fermentation conditions. For the purposes of the present invention, "modeling" a parameter refers to testing different values of that parameter. For example, liquefaction temperature can be modeled using the methods disclosed herein, i.e., the amount of ethanol resulting from liquefaction and subsequent fermentation of starch-containing plant material at various liquefaction temperatures can be assessed. Any parameter (or combination of parameters) that can be varied in a starch-to-ethanol conversion process (herein referred to as a "conversion process") can be modeled using the methods of the present invention. While not intending to provide an exhaustive list, parameters such as the source and type of plant material; the method of pretreatment (i.e., "processing"); the moisture content of the raw and/or processed plant material; the time, temperature, pressure, and/or pH used in any step of the conversion process; the source, type, and number of different enzymes used in any step of the conversion process; and, the type of organism used in the fermentation step can be modeled.

For example, the process can be modeled to increase the percentage of solids used to create the mash; to remove the addition of pH adjusting chemicals to the mash; to decrease the liquefaction time; to remove the use of a jet cooker; to alter the enzyme cocktails; to alter the form of the enzyme cocktail, and the like. If the desired parameter model is viscosity of the mash, then this viscosity can be determined using an RVA-4 Viscometer. If the model parameter is pH, then the ethanol production can be tested. The method for modeling can include the use of additional enzymes delivered either as transgenic plant material or delivered as a purified or semi-purified enzyme preparation (i.e., "liquid enzymes"). The additional enzymes can be additional starch-degrading enzymes, cellulases, pectinases or any other enzyme.

Thus, various parameters can be adjusted to improve the starch-to-ethanol conversion process. An improvement to this conversion process may include an improvement in the quality and/or quantity of one or more by-products or end products of the conversion process (including, for example, a decrease in one or more undesired products and an increase in one or more desired fermentation products), improvement in the speed or efficiency of the process, a decrease in the cost or energy usage of the process, a decrease in the amount of materials required for the process, and the like.

In some embodiments, the modeling is to achieve a desired quantity and/or quality of a product of the conversion process such as, but not limited to, alcohol, lactic acid, an amino acid, fructose, citric acid, propanediol, dried distiller grain, dried distiller grain and solubles. In some embodiments, the modeling may be used to learn about an oil, a protein, or a fiber by-product. These products can be primary (e.g., end products) or co-products (e.g., by-products) provided by the fermentation of a fermentable sugar. These products are collectively referred to herein as "fermentation products." The product can also be any product that can be recovered from any stage of a liquefaction, saccharification, and/or fermentation process. In each instance of model parameters, the implementation of the desired model parameters in a full scale ethanol production plant is envisioned.

In various embodiments, modeling of various parameters in the conversion process results in an increase in ethanol yield is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 3%, at least about 4%, at least about 5%, at least about 6%, at least about 7%, at least about 9% or greater than the ethanol yield using one or more alternative ethanol production processes. The comparison can be to conventional ethanol production processes or to another defined (e.g., reference) process. For example, the use of a particular starch-degrading enzyme may result in an increase in ethanol production compared to the amount of ethanol produced in a reference process using a different starch-degrading enzyme. Even small increases in ethanol yield will translate to large volumes of ethanol produced over time in a commercial-scale fermentation process.

Thus, in some model embodiments, the presently disclosed process produces a higher amount of ethanol than a reference process (e.g., than a conventional process). In some embodiments, the presently disclosed process produces ethanol more quickly during fermentation than a reference process. In some embodiments, fermenting the starch liquefact provides a solution comprising at least about 10% (w/v) ethanol after about 20 hours. In some embodiments, fermenting the starch liquefact provides a solution comprising at least about 11.8% (w/v) ethanol after about 96 hours.

In another embodiment, the methods disclosed herein result in a lower amount of residual sugar remaining after fermentation when compared to the amount of residual sugar remaining after fermentation of starch-containing plant material using a reference process. The amount of residual sugar can be reduced by at least about 1%, at least about 2%, at least about 3%, at least about 4%, at least about 5%, at least about 6%, at least about 7%, at least about 9%, at least about 10%, about 15%, about 20%, about 25%, at least about 30% or more. Residual sugar can be measured in terms of total carbohydrate levels or in terms of total glucose levels remaining after a certain period of time of fermentation.

The invention may be applied to plant material derived from any of a variety of plants, including, but not limited to *maize*, wheat, rice, barley, soybean, cotton, sorghum (milo), oats, beans in general, rape/canola, alfalfa, flax, sunflower, safflower, millet, rye, sugarcane, sugar beet, cocoa, tea, *Brassica*, cotton, coffee, sweet potato, flax, peanut, clover; grasses and trees; vegetables such as lettuce, tomato, cucurbits, cassava, potato, carrot, radish, pea, lentils, cabbage, cauliflower, broccoli, Brussels sprouts, peppers, and pineapple; fruits such as citrus, grapes, pineapple, apples, pears, peaches, apricots, walnuts, avocado, plantain, banana, and coconut; and flowers such as orchids, carnations and roses.

As used herein, the term "plant part," "plant material," or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The plant material can also be obtained as a previously treated plant product such as soy cake generated during the processing of soybeans. The plant material can be a mixture of such materials and by-products of such materials, e.g., corn fiber, corn cobs, stover, or other cellulose- and hemicellulose-containing materials, such as wood or plant residues. In various embodiments, the plant materials include corn, either standard corn, mutant corn, transgenic corn or waxy corn.

Following long-standing patent law convention, the terms "a" and "an" mean "one or more" when used in this application, including the claims. Thus, "an enzyme" or "a plant material" can refer to a plurality (i.e., two or more) enzymes or plant materials. As used herein, the term "about" modifying any amount can refer to the variation in that amount encountered in real world conditions of producing sugars and ethanol, e.g., in the lab, pilot plant, or production facility. Unless otherwise indicated, all numbers expressing quantities of percentage, weight, temperature, flow rate, time, pH, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

Processing

An initial step in the conversion process may include a pretreatment or "processing" step. Plant material can be initially processed by a variety of milling methods including but not limited to wet milling, dry milling, dry grinding, cracking, coarse grinding, fine grinding, fractionating, mixing, flaking, steam flaking, rolling or chopping. For example, plant material, such as kernels of corn, can be ground with a ball mill, a roller mill, a hammer mill, or another mill known for grinding plant material for the purposes of particle size reduction. The use of emulsion technology, rotary pulsation, and other means of particle size reduction can be employed to increase surface area of plant material while raising the effectiveness of flowing the liquefied media. To improve throughput and efficiency, the type of device used to process the plant material should be simple to use and simple to clean between grinding of successive samples.

The corn wet milling process separates corn into its four basic components: starch, germ, fiber and protein. There are four basic steps to accomplish this process. First the incoming corn is steeped to begin hydrolyzing the starch and breaking the protein bonds. The next step in the process involves a coarse grind to separate the germ from the rest of the kernel. The remaining slurry consisting of fiber, starch and protein is finely ground and screened to separate the fiber from the starch and protein. The starch is separated from the remaining slurry. The processed plant material can be referred to as being or including "raw starch."

In dry milling, the corn is combined with water in a brief tempering process prior to grinding the corn to a flour. The ground corn flour is then fractionated into bran, germ and grits (starchy fractions).

In dry grinding, the entire corn kernel or other starchy grain is first ground into flour, which is referred to in the industry as "meal" and processed without separating out the various component parts of the grain. The meal is slurried with water or backset to form a "mash."

Thus, it is envisioned that embodiments of the invention can be used in conjunction with any milling technique (including, but not limited to, wet milling, dry milling, dry grinding, cracking, coarse grinding, fine grinding, fractionating, mixing, flaking, steam flaking, rolling or chopping). However, it is also envisioned that plant material that has been minimally processed or is unprocessed can be used in the methods disclosed herein.

The starting amount of plant material necessary for the methods disclosed herein will vary, but it will generally be significantly less than the amount of starting material necessary to evaluate ethanol production in a full-scale conversion process. In fact, an advantage of the present invention is that model parameters can be evaluated when the availability of starting material is limited. In some embodiments, the amount of processed or unprocessed plant material used in the liquefaction step is less than about 10 grams, less than about 9 grams, less than about 8, 7, 6, 5, 4, 3, 2, or less than about 1 gram of material.

The processed sample material may then be subjected to a first NIR analysis step 110 in which a first NIR signal may be collected by a near infrared analytical device for use in building a calibration model for evaluating ethanol yield of biological material.

Drying

In a drying step 120, the processed or unprocessed plant material is driven to a desired moisture content prior to liquefaction. In one embodiment, the plant material is driven to a moisture content of less than about 20% (by weight), less than about 18%, less than about 15%, less than about 14%, less than about 13%, less than about 12%, less than about 11%, less than about 10%, less than about 9%, less than about 8%, less than about 7%, less than about 6%, or less than about 5% moisture. Drying all samples to a terminal moisture content prior to liquefaction eliminates the need to recalculate ethanol content based on the moisture level, thus increasing the efficiency of the process and accuracy of the ethanol measurement. By "terminal moisture" is intended a moisture content of less than about 5-8% by weight of the plant material. The goal is to have all samples within 1.5% of the moisture of the other samples. Drying all samples to a terminal moisture content prior to liquefaction eliminates the need to recalculate ethanol content based on the moisture level, thus increasing the efficiency of the process and accuracy of the ethanol measurement. In a preferred embodiment, the "terminal moisture" is intended to be a moisture content of between about 5% and 8% by weight of the plant material.

In the methods of the present invention, all samples are driven to a particular moisture content (e.g., terminal moisture) using a drying cabinet or similar device capable of maintaining a relative humidity within the range of the desired moisture content. The use of a drying cabinet eliminates the need to perform moisture analysis on each individual sample, which also increases the efficiency of the method. In one embodiment, the relative humidity (RH) of the drying cabinet (i.e., "desiccating" cabinet) is maintained from about 5% to about 20%, or any range in between 5% and 20% including, for example, from about 5%, 6%, 7%, 8%, 9%, 10%, 11%, or 12% to about 13%, 14%, 15%, 16%, 17%, 18%, 19%, or 20% RH.

To facilitate drying of the samples, the temperature of the drying cabinet is maintained at about 20° C. to about 35° C., or any range in between about 20° C. and about 35° C. including, for example, about 21° C., about 22° C., about 23° C., about 24° C., about 25° C., about 26° C., about 27° C., about 28° C., about 29° C., about 30° C., about 31° C., about 32° C., about 33° C., or about 34° C. It is also envisioned that the moisture content of the starch-containing plant material, as well as the temperature at which this moisture content is achieved, can be modeled using the platform disclosed herein.

In various embodiments, after drying of the processed or unprocessed samples, a specific amount of each sample is weighed in a moisture-controlled glove box preferably using an automated sample-dispensing unit. The RH of the glove box is maintained from 0-20%, and a dry inert gas (e.g., nitrogen or helium) is used in the glove box. The sample-dispensing unit increases throughput and the use of the glove box limits exposure of the samples to atmospheric moisture. The use of the glove box also limits interaction of the user with the plant material, reducing the probability of an allergic reaction.

After completion of drying step 120, the dried sample material may then be subjected to a second NIR analysis step 130 in which a second NIR signal may be collected by the near infrared analytical device for use in building a calibration model for evaluating ethanol yield of biological material.

Liquefaction

The next step in the conversion process involves the hydrolysis of starch, often mediated by one or more starch-degrading enzymes. The term "hydrolysis" is defined as a chemical reaction or process in which a chemical compound is broken down by reaction with water. The starch digesting enzymes hydrolyze starch into smaller units as previously described. Typical corn-to-ethanol conversion processes comprise liquefying an aqueous slurry of starch-containing plant material in the presence of one or more starch-degrading enzymes, e.g., α-amylase enzymes. The term "slurry" refers to a mixture of starch or a starch-containing material (e.g., milled corn) and an aqueous component, which can include, for example, water, deionized water, or a process water (i.e., backset, steam, condensate), or any combination thereof. The addition of water, enzyme, or other necessary nutrients or antibiotics to the plant material is typically performed using an automated dispensing unit, e.g., a robotic pipetting device. Use of this type of automated dispensing unit reduces the variability associated with hand-held devices such as pipetters, while also increasing throughput.

The liquefaction reaction involves heating a combination of ground grain and water beyond the grains' gelatinization point under slightly acidic conditions in the presence of an enzyme that will hydrolyze the linkage between the glucose units rendering a complex mixture of dextrins, sugars and other retrograde products. In order to facilitate wetting or mixing of the aqueous slurry, the liquefaction process can include an initial step of holding the slurry in a container (i.e., a pre-slurry container) for a period of time prior to the heating step. As used herein the terms "liquefaction," "liquefy," "liquefact," and variations thereof refer to the process or product of converting starch to soluble dextrinized substrates (e.g., smaller polysaccharides). Liquefact can also be referred to as "mash."

The methods used for liquefaction of an aqueous slurry of starch-containing plant material vary depending, in part, on the nature of the starch-degrading enzymes used in the process as well as the intended downstream use of the intermediate and end products. The steps can involve a single liquefaction step, or may involve a primary liquefaction, followed optionally by jet cooking and then a secondary liquefaction. The term "secondary liquefaction" refers to a liquefaction process that takes place after an initial period of liquefaction or after a jet cooking step of a multi-stage liquefaction process.

The conditions under which each step is performed also depends on the nature of the enzymes employed. For example, various starch-degrading enzymes have different degrees of thermostability and different requirements for pH. The steps should be performed under conditions sufficient for each type of starch-degrading enzyme employed in the process to hydrolyze the starch-containing plant material.

A common enzymatic liquefaction process involves adjusting the pH of a starch slurry to the pH optimum of the starch-degrading enzyme(s) employed in the methods, with the addition of calcium hydroxide, sodium hydroxide or sodium carbonate. The addition of calcium hydroxide has the advantage of also providing calcium ions which are known to stabilize certain starch-degrading enzymes against inactivation.

In another variation to the liquefaction process, a starch-degrading enzyme (e.g., α-amylase) is added to the starch suspension, the suspension is held at a temperature of 80-100° C. to partially hydrolyze the starch granules, and the partially hydrolyzed starch suspension is heated to temperatures in excess of about 105° C. to thoroughly gelatinize any remaining granular structure. After cooling the gelatinized starch, a second addition of the enzyme can be made to further hydrolyze the starch.

Yet another variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. A practice in the art is to undertake enzymatic liquefaction at a lower temperature when using the dry milling process.

In some embodiments, jet cooking could be desired. Thus, in some embodiments, the process further comprises a jet cooking step following the heating step. In some embodiments, the jet cooking comprises heating the slurry to a temperature ranging from about 90° C. to about 120° C. for a period of time ranging from about 3 minutes to about 15 minutes.

Following gelatinization, the starch solution may be held at an elevated temperature in the presence of a starch-degrading enzyme until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Fermentable sugar can be lost during high temperature, long hold times, and the use of only mildly acidic pH conditions. These losses can be attributed, at least in part, to Maillard reactions between a reducing end on the carbohydrate and an amino compound (e.g., ammonia or a protein). The Maillard reactions are known to be temperature, pH, and time dependent. Thus, various parameters can be modeled in the liquefaction step to achieve optimal starch-to-ethanol conversion.

At each step, the process can be modeled for a pH that is optimal for the particular enzyme(s) being employed in that step. In some embodiments, this slurry has a pH of between about 3.8 and about 5.2, including about 4.0, about 4.2, about 4.4, about 4.6, about 4.8, and about 5.0. In some embodiments, the pH is about 4.8. Reducing the pH from the 5.8 typical for liquefaction to a lower pH (e.g., between 5.2 and 3.8) should decrease the amount of Maillard reaction products.

In one embodiment, the process of starch liquefaction is modeled at a low pH, for example, the natural pH of a slurry comprising a milled starch-containing plant material and water. In this modeling, the starch liquefaction is performed at a lower pH, therefore no pH adjustment is necessary, either as part of liquefaction step or at any point during an ethanol production process involving a liquefaction step (i.e., throughout the combination of liquefaction, saccharification, and fermentation steps used to produce ethanol). Thus, no pH-adjusting materials (e.g., bases or salts) are added to the slurry.

The heating step of the liquefaction process can be modeled to involve the use of temperatures below those used during conventional liquefaction processes (e.g., below about 95° C. to 120° C.). In some embodiments, the liquefaction temperature ranges from about 60° C. to about 90° C. In some embodiments, the liquefaction temperature ranges from about 80° C. to about 90° C. In other embodiments, the liquefaction does not include a jet-cooking step. In some embodiments, the liquefaction does not include a secondary liquefaction step. Thus, the presently disclosed liquefaction method, in some embodiments, involves a single heating step, or no heating step at all. The temperature can be chosen to be compatible with thermostable glucoamylases, such as those derived from *Thermomyces lanuginosus* (i.e., *Thermomyces lanuginosus* glucoamylase).

Decreasing the time the slurry is held at high temperature should also decrease undesired degradation reactions. Thus, in various embodiments, the period of time for each liquefaction step can be less than about 180 minutes. In some embodiments, the period of time for each liquefaction step ranges from about 2 minutes to about 200 minutes, including from about about 5, about 10, about 15, about 20, about 25, about 30, about 11, about 12, about 13, about 14, about 15, about 16, about 17, about 18, about 19, about 35, about 40, about 45, about 50, about 60, about 70, about 80, about 90, about 100, about 100, about 110, about 120, about 130, about 140, about 150, about 160, about 170, about 180, or about 190 minutes. In some embodiments, the period of time ranges from 60 minutes to about 150 minutes. It is envisioned that the period of time for each liquefaction step can be modeled for any period of time.

In various embodiments of the invention, each of the liquefaction steps is performed in a convected oven set at the desired temperature. Performing liquefaction in the oven eliminates the space requirements needed for water baths, increases throughput and reduces the risk of exposure of the operator to hot water. Performing the liquefaction in a single oven also reduces the temperature variation that is present between and within conventional water baths. This technique is successfully used with the small-volume headspace vials since the mass transfer of heat is greatly reduced with the small liquefacts. It will be understood that use of this technique with larger liquefact volumes will require longer residence times in the liquefaction oven.

Saccharification

An optional step in the starch-to-ethanol conversion process involves saccharification of the starch liquefact. As used herein, the terms "saccharification" and "saccharifying" refer to the process of converting polysaccharides to dextrose monomers using enzymes. Saccharification can specifically refer to the conversion of polysaccharides in a liquefact. Saccharification products are, for example, glucose and other small (low molecular weight) oligosaccharides such as disaccharides (a DP2) and trisaccharides (a DP3). The saccharification step can include adding one or more starch-degrading enzymes to the starch liquefact during liquefaction (simultaneous liquefaction and saccharification, SLS) or after liquefaction. In some embodiments, the additional starch-degrading enzymes include glucoamylase.

The amount of glucoamylase employed in the present process can vary according to the mixture of dextrins present in the starch liquefact. For example, if the starch liquefact is high in concentration of fermentable, small sugars, less glucoamylase might be needed.

The saccharification process can further include a heating step, wherein the starch liquefact comprising additional starch-degrading enzymes (i.e., the saccharification mixture) is heated to a temperature (e.g., a temperature that allows for optimal activity for the enzymes employed) for a period of time. For example, the starch liquefact can be heated in the presence of an additional starch-degrading enzyme (e.g., glucoamylase) for a period of time from about 5 minutes to about 90 minutes at a temperature from about 60° C. to about 75° C. The temperature can be chosen to be compatible with thermostable glucoamylases, such as those derived from *Thermomyces lanuginosus* (i.e., TlGA).

In some embodiments, the heating step effects complete saccharification of the slurry. Thus, in some embodiments, approximately 100% of the glucose expected from hydrolysis of the starch in the slurry is produced during the heating step. In some embodiments, the heating step effects partial saccharification of the slurry. For example, heating can lead to a mixture containing at least some glucose and some larger dextrins.

In some embodiments, the process can include a separate second saccharification step. For example, the process can comprise heating the mixture containing glucose to a second temperature for a second period of time, thereby effecting complete saccharification of the mixture. This second heating step can include the addition of additional enzyme, e.g., additional glucoamylase.

In some embodiments, the mixture from a partial SLS process can be used in a fermentation wherein additional saccharification can take place during fermentation. Thus, in some embodiments both additional enzymes and yeast can be added to the mixture, thereby producing additional glucose and producing ethanol. In some embodiments, the glucose of the presently disclosed process can be used to produce an end product selected from the group consisting of an alcohol, lactic acid, an amino acid, fructose, citric acid, propanediol, DDG, DDGS, or a combination thereof.

The glucose produced from a complete simultaneous liquefaction and saccharification process can also be modeled. In addition to glucose, the heated mash can comprise additional materials, such as oil, protein and fiber by-products of the simultaneous liquefaction and saccharification process. These materials can also have economic value and can be recovered as well.

Subsequent modeling of fermentation of a partially saccharified mixture can be advantageous, in that it allows for modeling the control of the initiation, rate, and/or extent of fermentation activity during a SSF process. In particular, the quantity of different starch-containing plant materials and or enzymes can be adjusted to provide a suitable amount of glucose to enhance the survival of yeast during a subsequent fermentation of the mixture resulting from the simultaneous liquefaction and saccharification process. The amount of glucose being fed into a fermentation process can also affect the quality of co-products of the fermentation process, including dried distiller grain and dried distiller grain and solubles.

Starch-degrading Enzymes

As discussed supra, one or more steps of the conversion process employs one or more starch-degrading enzymes, and the type, amount, and source of enzymes can be modeled using the platform described herein. The term "starch-degrading enzyme" includes any enzyme that can catalyze the transformation of a starch molecule or a degradation product of a starch molecule. Starch-degrading enzymes can be added to the starch hydrolysis process as either a purified or semi-purified enzyme preparation (i.e., liquid or dry enzyme) added when the processed plant material is mixed with water or can be delivered by using transgenic plant material expressing the starch-degrading enzyme as described in US patent application US2003/0135885 (herein incorporated by reference in its entirety). Transgenic plant material expressing a starch-degrading enzyme can be combined with at least one other starch-containing plant material to form an admix such that the transgenic plant material delivers an appropriate amount of starch-degrading enzyme to perform the starch hydrolysis process.

The different plant materials may be combined by one or more process, including but not limited to, wet milling, dry milling, dry grinding, cracking, coarse grinding, fine grinding, fractionating, mixing, flaking, steam flaking, rolling and chopping. The admix can be formed by mixing dry plant materials from different starch-containing plants together before wetting with the aqueous solution. It is also possible to form a mash by adding the different starch-containing plant materials sequentially or simultaneously to a vessel while an aqueous solution is being added. Any suitable mixing method can be used, including any suitable manual or mechanical mixing method that can be used in conjunction with the pre-slurry, slurry and liquefaction. However, to increase consistency and speed of the process, a high speed/high throughput shaker is typically used. The utilization of this type of shaker reduces the variation associated with shaking samples by hand, using multiple stir plates or using multiple orbital shakers.

Starch-degrading enzymes suitable for the present invention include starch-degrading or isomerizing enzymes including, for example, $\alpha$-amylase (EC 3.2.1.1), endo or exo-1,4- or 1,6-$\alpha$-D-glucoamylase, glucose isomerase, $\beta$-amylases (EC 3.2.1.2), $\alpha$-glucosidases (EC 3.2.1.20), and other exo-amylases; starch debranching enzymes, such as isoamylase (EC 3.2.1.68), pullulanase (EC 3.2.1.41), neo-pullulanase, isopullulanase, amylopullulanase and the like; glycosyl transferases such as cyclodextrin glycosyltransferase and the like. Starch-degrading enzymes can be used in conjunction with other enzymes that can facilitate the release of starch from plant tissue. Starch-degrading enzymes can be used in conjunction with cellulases such as exo-1,4-$\beta$-cellobiohydrolase (EC 3.2.1.91), exo-1,3-$\beta$-D-glucanase (EC 3.2.1.39), hemicellulase, $\beta$-glucosidase and the like; endoglucanases such as endo-1,3-$\beta$-glucanase (EC 3.2.1.6) and endo-1,4-$\beta$-glucanase (EC 3.2.1.4) and the like; L-arabinases, such as endo-1,5-$\alpha$-L-arabinase (EC EC 3.2.1.99), $\alpha$-arabinosidases (EC 3.2.1.55) and the like; galactanases such as endo-1,4-$\beta$-D-galactanase (EC 3.2.1.89), endo-1,3-$\beta$-D-galactanase (EC 3.2.1.90), 1-galactosidase, $\alpha$-galactosidase and the like; mannanases, such as endo-1,4-$\beta$-D-mannanase (EC 3.2.1.78), $\beta$-mannosidase (EC 3.2.1.25), $\alpha$-mannosidase (EC 3.2.1.24) and the like; xylanases, such as endo-1,4-1-xylanase (EC 3.2.1.8), $\beta$-D-xylosidase (EC 3.2.1.37), 1,3-$\beta$-D-xylanase, and the like; pectinases and phytases. In some embodiments, the starch-degrading enzyme is $\alpha$-amylase, pullulanase, $\alpha$-glucosidase, glucoamylase, amylopullulanase, glucose isomerase, or combinations thereof.

The starch-degrading enzyme or combination thereof can be modeled based on the desired starch-derived end product, the end product having various chain lengths based on, e.g., a function of the extent of processing or with various branching patterns desired. For example, an $\alpha$-amylase, glucoamylase, or amylopullulanase can be used under short incubation times to produce dextrin products and under longer incubation times to produce shorter chain products or sugars. A pullulanase can be used to specifically hydrolyze branch points in the starch yielding a high-amylose starch, or a neopullulanase can be used to produce starch with stretches of α-1,4 linkages with interspersed α-1,6 linkages. Glucosidases can be used to produce limit dextrins, or a combination of different enzymes can be used to make other starch derivatives. In some embodiments, a glucose-isomerase can be selected to convert the glucose (hexose) into fructose.

Alpha-amylase refers to an enzyme which cleaves or hydrolyzes internal α (1-4) glycosidic bonds in starch to produce α 1-2 bonds, resulting in smaller molecular weight maltodextrins. These smaller molecular weight maltodextrins include, but are not limited to, maltose, which is a disaccharide (i.e., a dextrin with a degree of polymerization of 2 or a DP2), maltotriose (a DP3), maltotetrose (a DP4), and other oligosaccharides. The enzyme α-amylase (EC 3.2.1.1) can also be referred to as 1,4-α-D-glucan glucanohydrolase or glycogenase. A variety of α-amylases are known in the art and are commercially available. An α-amylase can be from any organism including plant, fungi, and bacteria, and can be expressed in transgenic plants. The α-amylase can be thermostable. The alpha-amylase can be 797GL3.

Glucoamylase (also known as amyloglucosidase) refers to the enzyme that has the systematic name 1,4-α-D-glucan glucohydrolase (E.C. 3.2.1.3). Glucoamylase removes successive glucose units from the non-reducing ends of starch. A variety of glucoamylases are known in the art and are commercially available. For example, certain glucoamylases can hydrolyze both the linear and branched glucosidic linkages of starch, amylose, and amylopectin. Glucoamylase can be from any organism including plant, fungi, and bacteria, and can be expressed in transgenic plants. The glucoamylase can be thermostable.

The type, amount, and/or source of starch-degrading enzyme can be modeled using the methods of the present invention. For example, enzymes having different substrate specificities, temperature optima, thermal tolerance, stability, pH requirements, and the like can be tested alone or in various combinations for improvements in the starch-to-ethanol conversion process. In one embodiment, the amount of glucoamylase is modeled according to the mixture of dextrins present in the starch liquefact. For example, if the starch liquefact is high in concentration of fermentable, small sugars, less glucoamylase might be needed.

Fermentation

Following liquefaction, saccharification, or SLS, the resulting hydrolyzed sugars and starch are subjected to a fermentation step 140. "Fermentation" or "fermenting" refer to the process of transforming sugars from reduced plant material to produce alcohols (e.g., ethanol, methanol, butanol, propanol); organic acids (e.g., citric acid, acetic acid, itaconic acid, lactic acid, gluconic acid, propionate); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Fermentation can include fermentations used in the consumable alcohol industry (e.g., beer and wine), dairy industry (e.g., fermented dairy products), leather industry, and tobacco industry. Thus, fermentation includes alcohol fermentation. Fermentation also includes anaerobic fermentations.

In one embodiment, the capacity and efficiency of the process is improved by performing fermentation reactions in small, preferably single-use, vials (e.g., small-volume headspace vials, such as 20 ml headspace vials). Performing the fermentations in small-volume vials significantly increases the number of simultaneous fermentation reactions that can be performed compared to methods using larger vessels. Space requirements for the fermentations are greatly reduced. Furthermore, single-use vials reduce the time and effort required to wash glassware.

Fermentation can be accomplished by any organism suitable for use in a desired fermentation step. Suitable fermenting organisms are those that can convert DP1-3 sugars, especially glucose and maltose, directly or indirectly to the desired fermentation product (e.g., ethanol, propanol, butanol or organic acid). Fermenting can be effected by a microorganism, such as fungal organisms (e.g., yeast or filamentous fungi). The yeast can include strains from a *Pichia* or *Saccharomyces* species. The yeast can be *Saccharomyces cerevisiae*. Bacterial can also be used in a fermentation process. Bacteria include but are not limited to species from *Acetobacter*, engineered *E. coli, Clostridium, Acidofilous* or *Lactobacter*. The selection of yeast can be modeled using the methods disclosed herein. Further, the amount of yeast employed can be modeled to effectively produce a desired amount of ethanol in a suitable time.

In some embodiments, the fermentation step involves a simultaneous saccharification and fermentation (SSF) step. In yet another embodiment, the starch-containing plant material may be used in raw starch fermentation. In the raw starch fermentation, the starch is not liquefied before enzymatic hydrolysis, and the hydrolysis is carried out at a temperature below gelatinization simultaneously with the fermentation process.

In some embodiments, the fermentation step comprises adding a solution of yeast to the cooled starch liquefact or raw starch and agitating the cooled starch liquefact at a temperature from about 28° C. to about 35° C. for a period of time sufficient for conversion of a sufficient quantity of the sugars to ethanol, e.g., from about 12 to about 72 hours. In some embodiments the yeast is Ethanol Red yeast.

The saccharification and/or fermentation mixture can include additional ingredients to increase the effectiveness of the process and it will be understood that any of these ingredients can be modeled to improve the starch-to-ethanol conversion process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like. In some embodiments, the process comprises adding one or more reagents from the group consisting of an additional starch-degrading enzyme, a yeast extract, an antibiotic, and yeast to the starch liquefact.

In an embodiment, fermentation is conducted for about 12 to about 96 hours, for example from about 18 to about 72 hours, about 24 to about 72 hours, about 48 to about 72 hours, or about 48 to about 96 hours. For example, fermentation can be conducted for about 12, about 18, about 24, about 30, about 36, about 42, about 48, about 54, about 60, about 66, about 72, about 78, about 84, about 90, or about 96 hours. In an embodiment, fermentation is conducted at a temperature of about 25° C. to about 40° C., or about 30° C. to about 35° C.

To stop the fermentation process, the samples are pasteurized in a convected oven set at 80-90° C. for a period of 40-60 minutes. The use of pasteurization limits exposure to acids used to stop the fermentation in a conventional process and eliminates corrosive acids from being injected into devices used to measure products of the conversion process. This technique is successfully used with the small-volume headspace vials since the mass transfer of heat is greatly reduced with the small ferments. It will be understood that use of this technique with larger fermentation volumes will require longer residence times in the pasteurization oven. Use of pasteurization is preferred over the alternative of not stopping the fermentation, which creates variation between fermentation times of samples being prepared for analysis.

As noted elsewhere herein, in some embodiments, the entire ethanol producing process can be modeled to have no pH adjustment. Thus, in some embodiments, no salts are added during saccharification and/or fermentation. Eliminating pH adjustments can reduce the costs of purchasing and storing chemicals and can reduce the salt content of the intermediates (e.g., glucose) produced. The elimination of calcium containing salts can reduce the formation of "beer stone" and the costs associated with its removal.

Analysis of Ethanol Production

In conventional ethanol conversion processes, the production of ethanol is monitored or the amount of ethanol is measured using high-performance liquid chromatography (HPLC), which requires time-consuming sample preparation steps. While the use of HPLC is not specifically excluded for measuring certain by-products or end products of starch-to-ethanol conversion, a preferred method for measuring ethanol production is headspace analysis, preferably using gas chromatography. The "headspace" is the gas space in a vial above the sample. Headspace analysis is, therefore, the analysis of the components present in that gas. Headspace analysis makes use of the dynamic equilibrium existing at a given temperature and pressure between ethanol in liquid and vapor phases within the fermentation vial. In this manner, a reference measurement may be determined/collected in step 150, which may then used in forming a correlation (step 160) to the first and second NIR signals collected from the near infrared analytical device. As such, a calibration model may be built in a rapid and efficient manner through implementation of method 100 such that the calibration model can be used in evaluating ethanol yield in ethanol producing material substantially similar in composition as those used to build the calibration model.

Headspace gas chromatography (HSGC) generally consists of a static or dynamic headspace gas sampling device, which may be manually operated or automated, and a gas chromatograph (GC). The ethanol concentration of the headspace air is determined by sampling a portion of the vial headspace and analyzing the headspace sample with a GC. This step is typically performed automatically using an auto-sampling system. A representative fraction or the total amount of the volatile components is carried into the chromatographic column mounted in the oven of a gas chromatograph.

Several devices are commercially available, including devices with dual injectors for analysis of two samples at the same time. Dynamic headspace sampling devices usually preconcentrate a representative fraction or the total amount of the volatile components of the test sample in a trap. The representative fraction or the total amount of the preconcentrated volatile components of the test sample is then carried from the trap into the chromatographic column mounted in the oven of a gas chromatograph. A flow of carrier gas carries the volatile components through the chromatographic column where they are separated. The separated components enter a detector, which determines the concentration or mass flow of the components in the carrier gas.

Post-fermentation Solids

Following fermentation, the remaining stillage includes both liquid and solid materials that are of commercial value. In particular, dried distiller grain and dried distiller grain and solubles are economically important co-products of corn-to-ethanol production. Dried distiller grain and dried distiller grain and solubles are primarily used as animal feed. The thin stillage can be concentrated to a syrup, which can be added to the dried distiller grain and the mixture then dried to form distiller's dried grain plus solubles (dried distiller grain and solubles). Thus, the process of the invention can be modeled to improve the quality and/or quantity of these end products. Recognized value attributes of dried distiller grain and solubles include consistency, physical characteristics (e.g. flowability, color, odor), and composition (e.g. protein and fiber content). Improvements in dried distiller grain and solubles benefit ethanol producers, commodity marketers, and the animal production industry.

The quality of dried distiller grain and dried distiller grain and solubles is negatively impacted by prolonged process time and elevated temperature. Maillard reaction products are formed during high temperature process steps in conventional corn-to-ethanol productions. The presence of Maillard reaction products negatively impacts the quality of dried distiller grain and dried distiller grain and solubles. As discussed supra, the presently disclosed process can be modeled to result in reduced process time, reduced process temperature, or both. This, in turn, can reduce formation of Maillard reaction products and thus improve the consistency and physical characteristics of the dried distiller grain and dried distiller grain and solubles.

Source of Plant Material

Starch-containing plant material useful in the methods of the present invention can be derived from a transgenic or a nontransgenic plant. As used herein the term "transgenic" refers to plants that include a heterologous polynucleotide. A heterologous polynucleotide can be a polynucleotide isolated from one species and then transferred back into the same species or a different species. The term "transgenic plant" can refer either to the initially transformed plant or to the progeny of the initially transformed plant. Techniques for transforming plants, plant cells or plant tissues can include, but are not limited to, transformation with DNA employing *A. tumefaciens* or *A. rhizogenes* as the transforming agent, electroporation, DNA injection, microprojectile bombardment, and particle acceleration. See, for example, EP 295959 and EP 138341.

The starch-containing plant material used herein may be an admixture of different types of plant materials. The term "admix" or "admixture" refers to a combination of elements. For example, an admix of plant material can refer to mixing two or more plant materials together to form a mixture. It is possible to further define the admixture by indicating the percentage of one or more of the elements. The plant material can be comprised of nontransgenic material or both transgenic and non-transgenic plant or just transgenic material. Transgenic plant material can contain a heterologous transgene encoding an enzyme, an insect control gene, an herbicide tolerance gene, a phytase, a nematode control gene or any other transgenic gene. The transgenic material may express more than one transgene.

The starch-containing plant material can be from a source (e.g., a plant strain) that is known to produce a relatively high level of fermentable sugars upon liquefaction and/or saccharification, or that has been bred or engineered to have some other advantageous property (e.g., pest or drought resistance). In some embodiments, more than two starch-containing plant materials can be used. Any combination of transgenic and nontransgenic plants can be used.

The ratio of non-starch-degrading enzyme-expressing plant material and starch-degrading enzyme-expressing plant material can be modeled in any suitable ratio so that the amount of starch-degrading enzyme in the mash is sufficient to digest the starch to produce glucose in a suitable amount of time or to produce a mixture that contains a desired level of glucose. Similarly, the ratio of the different starch-degrading enzyme-expressing plant materials can be modeled to facilitate a desired amount of saccharification in a desired amount of time.

Source of Starch-degrading Enzymes

In the starch-to-ethanol conversion process disclosed herein, the starch-degrading enzyme(s) can be provided in the slurry as transgenic plant material expressing one or more starch-degrading enzymes, may be provided as a purified or semi-purified enzyme preparation and exogenously added to the slurry, or may be provided in any combination thereof. Where multiple starch-degrading enzymes are employed, the slurry may comprise an admixture of a first starch-containing plant material expressing at least a first starch-degrading enzyme, and a second starch-containing transgenic plant material that expresses a second starch-degrading enzyme. Alternatively, the different starch-degrading enzymes can be expressed from a single variety of plant that expresses each starch-degrading enzyme through transformation or breeding. The admixture may further comprise starch-containing plant material that does not express any starch-degrading enzyme. Likewise, the admixture may comprise transgenic starch-containing plant material expressing only one starch-degrading enzyme (where the second starch-degrading enzyme is added exogenously to the slurry) or may consist only of starch-containing plant material that does not express a starch-degrading enzyme (where each starch-degrading enzyme is added exogenously to the slurry). The slurry can further comprise an aqueous solution (e.g., water, de-ionized water, backset (i.e., stillage), etc.).

Where one type of starch-degrading enzyme is provided as transgenic plant material, and another type of starch-degrading enzyme is provided exogenously as a purified or semi-purified enzyme preparation, the initial liquefaction steps may be performed under conditions compatible with the transgenically-expressed starch-degrading enzyme. The exogenous starch-degrading enzyme can be added to the slurry during the initial liquefaction steps if the enzyme has similar thermostability and pH optimum characteristics as the transgenically-expressed starch-degrading enzyme.

Alternatively, the exogenous starch-degrading enzyme can be added in a secondary liquefaction step. This secondary liquefaction step should be performed under conditions sufficient for the exogenous starch-degrading enzyme to hydrolyze the starch-containing material, which may or may not require adjustment of the pH and/or ion concentrations of the slurry.

Where two or more types of starch-degrading enzymes are added to the slurry exogenously, the liquefaction steps should be compatible with both types of enzymes, and may require separate liquefaction steps with adjustment of pH and/or ion concentrations between the steps. One of skill in the art will recognize that the pH, ion concentration, temperature, and length of time for each step can be optimized according to the type of starch-degrading enzyme(s) employed in the liquefaction as well as the products desired from the liquefaction. Likewise, the pH, ion concentration, temperature, and length of time for each liquefaction step can be modeled to improve production of ethanol and/or by-products or end products of the starch-to-ethanol conversion process. Exemplary, non-limiting liquefaction methods are provided elsewhere herein.

In some embodiments, dry plant materials from different starch-containing plants are mixed together before wetting with the aqueous solution. In other embodiments, the different starch-containing plant materials are added sequentially or simultaneously to a vessel while an aqueous solution is being added. In some embodiments, the different plant materials can be grown together in a pre-determined ratio to provide a harvestable crop that can be used as the starch source for the presently disclosed process.

The following examples are offered by way of illustration and not by way of limitation.

EXPERIMENTS

The High Throughput Screening Platform is made up of a number of processes. Most of the experiments listed below followed this protocol unless noted otherwise in the experiment. The method steps may include a. grinding, b. drying corn flour, c. weighing flour, d. water, nutrient, antibiotic and enzyme addition, e. liquefaction, add fermentation cocktail, f. fermentation, stop fermentation, g. pasteurization, and h. headspace analysis via gas chromatography. The calculator for different components is based on g of dry flour and all liquefactions and fermentations are assembled accordingly. Therefore it is imperative that the percent moisture of corn flour be determined.

a) Grinding—standard disc mill grinder is used.
    b) Drying corn flour—the corn flour is driven to a terminal moisture level in a desiccating cabinet. The RH of the moisture cabinet may be from 5 to 20%, with a temperature range of 20 to 35° C.
    c) Weighing Flour—Corn flour is weighed in a moisture-controlled glove box using an automated flour-dispensing unit. The RH of the glove box is maintained from 0-20%.
    d) Addition of water, nutrient, antibiotic and enzymes—Each of the components listed are dispensed using computer controlled, repeating, dispensing units. Dispensing ranges are from 10 ul to 10 ml
    e) Liquefaction—performed at a temperature range of about 75 to 95 ° C. for about 1 to 2 hours.
    f) Fermentation—performed in 30±5° C. growth chambers. Ferments are allowed to grow for 24, 48 and 72 hours.
    g) Pasteurization—to stop the fermentation process, the samples are pasteurized in a convected oven set at 80-90° C. for a period of 40-60 minutes.
    h) Headspace analysis via gas chromatography—to analyze the samples ethanol content headspace GC analysis is utilized. The sample is incubated at 45±5° C. for 1.5 to 1.8 minutes. A headspace sample is then removed with a 46±5° C. heated syringe. The syringe then is injected into a 250±5° C. injection port, with a split flow of 25:1.

The sample components are separated on an Agilent DB-ALC1 column at an isothermic oven temperature of 75±5° C. with a column flow of 7.5±0.5 ml/min.

Experiment 1

Component Loss of Fermentation Components Due to Pasteurization Step in the HTS Fermentation Platform Research Objective Research Hypothesis: In order for the high throughput fermentation platform to provide accurate ethanol yield data, the ferment must be arrested prior to analysis. To arrest the ferment the yeast must be killed to prevent fermentation from occurring beyond the specific fermentation time point of interest. One way in which the yeast may be killed is to pasteurize the ferment, a method used in the brewing industry. Pasteurizing the ferments in the 20 ml headspace vials for a period of 45 minutes arrests the fermentation. Utilizing pasteurization as a method to kill the yeast may also cause loss of fermentation components due to evaporation. The hypothesis of this experiment is that the loss of any components due to evaporative loss is consistent across all headspace fermentation vials.

Technical Approach: One-hundred and eight (108) fermentations are conducted in 20 ml headspace vials. The fermentation is divided into 3 treatment groups with 36 replications per treatment. Table 1 summarizes the treatments.

TABLE 1

Sample Matrix Design for the Measurement of Evaporative Weight Loss

| Treatment | # of Replications | Length of Fermentation (hours) |
|---|---|---|
| 1 | 36 | 24 |
| 2 | 36 | 48 |
| 3 | 36 | 72 |

A total of 108 headspace vials containing ferments are arrested after fermenting 24, 48 and 72 hours. The headspace vials containing ferment are weighed prior to the pasteurization step and immediately afterwards to determine the mass loss due to evaporation.

Materials and Methods

| | |
|---|---|
| Yellow dent corn | Perten 3600 Disc Mill |
| Perten DA7200 | Urea 1 g/2 ml Stock |
| VWR incubator | Sigma *A. niger* Glucoamylase |
| 20 ml headspace vials | Analytical balance |
| Tetracycline (10 mg/ml in 50% EtOH stock solution). | Ethanol Tech AYF 1177 |
| Genencor Spezyme Xtra | Ethanol Tech SLY Yeast |
| Growth chamber | Fluid Management 5G HD Mixer |
| Despatch Forced Convected Bench-top Oven | Mettler Toledo AB135-S/FACT Balance |

Yellow dent corn was ground using a Perten 3600 Disc Mill, on setting 0.

Moisture content of the flour was measured using a Perten DA7200.

The "Liquefaction Fermentation calculator" was used to determine the appropriate amounts of yellow dent corn flour, water, and alpha amylase (Genencor's Spezyme Xtra) to achieve 30% dry solids and placed into 108 headspace vials for liquefaction.

Liquefactions were carried out in the Despatch convected oven at 85° C. for 90 minutes. During liquefaction, the vials were mixed every 20 minutes using the 5G HD mixer.

After the liquefaction the samples were cooled to ambient temperatures.

The "Liquefaction Fermentation calculator" was used to determine the appropriate amounts of glucoamylase, nutrient, antibiotic, and yeast to add to each sample.

The vials were mixed once again using the 5G HD mixer.

The samples were placed in the 30° C. growth chambers and allowed to ferment for 24, 48 or 72 hours. A small hole should be punctured in each cap for ventilation during fermentation.

Ninety (90) microliters of n-propanol alcohol is added to each vial at the end of each fermentation period.

The mass of each vial was determined using the Mettler balance. The initial mass was recorded.

The vials were placed in the Despatch convected oven at 85° C. for 45 minutes to pasteurize the samples At the end of the 45 minute pasteurization the vials were removed from the oven and allowed to cool to ambient temperature.

The final mass of the vials was then determined and recorded. The change in mass was determined for each vial using the formula:

$$\text{Mass Loss due to Pasteurization} = \text{Mass}_{(initial)} - \text{Mass}_{(final)}$$

Results and Discussion

The loss of mass due to the pasteurization step was consistent across the 3 fermentation periods. The mean losses for each fermentation period are the following: a) 24 hour fermentation=7.7 mg, b) 48 hour fermentation=5.3 mg, and c) 72 hour fermentation=6.5 mg. A single factor ANOVA was used to compare the 3 sample sets. There was no significant difference found (P=0.60) in the loss of mass between the sample sets.

The results of this experiment clearly indicate that the loss of volatile components due to the pasteurization step is consistent across the three fermentation periods. Adjustments for evaporative mass loss do not need to be made to ethanol data collected across the three fermentation periods. The results of this experiment also indicate that the mean loss of volatile components due to the pasteurization step is <0.1% of the 9 g ferments utilized on the high throughput fermentation platform.

Experiment 2

Waxy Near Isogenic Inbred Lines (NILS) Study

Research Objective

Research Hypothesis: This study hypothesizes that a near isogenic inbred line (NILS) of the waxy trait with 100% amylopectins will result in a faster accumulation of soluble dextrins as compared to non-waxy NIL corn, which in theory will result in a faster fermentation reaction in a high throughput dry grind process.

Technical Approach: 120 fermentations will take place in 20ml headspace vials. The 120 fermentations are divided into 2 treatments with 10 reps per time point for 2 *maize* lines. The time points are 24, 48, and 72 hours. The 2 treatments are: 1) 30% solids and 3) 36% solids. Table Sample Matrix of Waxy Near-Isogenic Lines Study summarizes the treatment groups.

TABLE

Sample Matrix of Waxy Near-Isogenic Lines Study

| Maize Lines | Pedigree | Solids | Time Point | Reps | Total |
|---|---|---|---|---|---|
| Waxy NIL | C9RA | 30, 36 | 24, 48, 72 hours | 10/solid/time point | 60 |
| Non-waxy NIL | C9 | 30, 36 | 24, 48, 72 hours | 10/solid/time point | 60 |
| | | | | Project Total | 120 |

Work Plan: The samples will be randomized in 1 day of fermentation (see Appendix B). Each sample will be fermented for 72 hours in the growth chamber at 30° C. At 24, 48, and 72 hours, samples will be prepared for ethanol analysis via GC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Genencor ® Spezyme Xtra | Ethanol Tech ® AYF1177 Nutrient |
| Distilled water | Tetracycline |
| Shaker | Oven |
| 20 ml headspace vials and caps | Growth Chamber |
| Analytical Balance | Powder handling system |
| Liquid handling system | Gas chromatography |

Moisture is measured on the sample using the Perten DA NIR7200.

Use the powder handling system to weigh 3 g of corn flour into each 20 ml headspace vial and cap each vial after weighing.

Use the "Dry-Grind Ethanol Calculator" and the moisture measured to determine the appropriate amounts of water and alpha amylase to achieve the necessary dry solids for each sample. Refer to Table Sample Matrix of Waxy Near-Isogenic Lines Study.

TABLE

Sample Matrix of Waxy Near-Isogenic Lines Study

| Maize Lines | Pedigree | Solids | Time Point | Reps | Total |
|---|---|---|---|---|---|
| Waxy NIL | C9RA | 30, 36 | 24, 48, 72 hours | 10/solid/time point | 60 |
| Non-waxy NIL | C9 | 30, 36 | 24, 48, 72 hours | 10/solid/time point | 60 |
| | | | | Project Total | 120 |

Dispense the liquids using the liquid handling system by piercing each vial cap.

Liquefactions are carried out in an oven at 85° C. for 90 minutes. During liquefaction, shake the sample three times; approximately every 20 minutes during the process.

After the liquefaction, samples are cooled to room temperature.

Use the "Dry-Grind Ethanol Calculator" to determine the appropriate amounts of glucoamylase, nutrient, antimicrobial, and yeast to achieve the necessary dry solids for each sample.

After addition of enzymes, set them to ferment at 30° C. in the growth chamber for 72 hours. A small hole should be punctured in each cap for ventilation during fermentation.

At 24, 48, and 72 hours, samples are prepared for ethanol analysis via GC.

Results and Discussion

| | | | | | | | | | |
|---|---|---|---|---|---|---|---|---|---|
| | | | | 24 hours data at 30% | | | | | |
| Variable | Line | N | Lower CL Mean | Mean | Upper CL Mean | Lower CL Std Dev | Std Dev | Upper CL Std Dev | Std Err |
| Ethanol | Nonwaxy | 10 | 6.56 | 6.76 | 6.96 | 0.19 | 0.28 | 0.51 | 0.09 |
| Ethanol | Waxy | 10 | 6.71 | 6.87 | 7.03 | 0.15 | 0.22 | 0.40 | 0.07 |
| Ethanol | Diff | | −0.35 | −0.11 | 0.13 | 0.19 | 0.25 | 0.37 | 0.11 |

| Variable | Method | Variances | DF | t Value | Pr > |t| | Significance |
|---|---|---|---|---|---|---|
| Ethanol | Pooled | Equal | 18 | −0.99 | 0.34 | |
| Ethanol | Satterthwaite | Unequal | 17.1 | −0.99 | 0.34 | |

| Variable | Method | Num DF | Den DF | F Value | Pr > F | Significance |
|---|---|---|---|---|---|---|
| Ethanol | Folded F | 9 | 9 | 1.58 | 0.50 | |

| | | | 24 hours data at 36% | | | | | |
|---|---|---|---|---|---|---|---|---|
| Variable | Line | N | Lower CL Mean | Mean | Upper CL Mean | Lower CL Std Dev | Std Dev | Upper CL Std Dev | Std Err |
| Ethanol | Nonwaxy | 10 | 6.25 | 6.49 | 6.74 | 0.24 | 0.35 | 0.63 | 0.11 |
| Ethanol | Waxy | 10 | 6.59 | 6.82 | 7.06 | 0.23 | 0.33 | 0.60 | 0.10 |
| Ethanol | Diff | | −0.65 | −0.33 | −0.01 | 0.25 | 0.34 | 0.50 | 0.15 |
| Variable | Method | Variances | DF | t Value | Pr > \|t\| | Significance | | | |
| Ethanol | Pooled | Equal | 18 | −2.2 | 0.042 | * | | | |
| Ethanol | Satterthwaite | Unequal | 18 | −2.2 | 0.042 | | | | |
| Variable | Method | Num DF | Den DF | F Value | Pr > F | Significance | | | |
| Ethanol | Folded F | 9 | 9 | 1.1 | 0.88 | | | | |

| | | | 48 hours data at 30% | | | | | |
|---|---|---|---|---|---|---|---|---|
| Variable | Line | N | Lower CL Mean | Mean | Upper CL Mean | Lower CL Std Dev | Std Dev | Upper CL Std Dev | Std Err |
| Ethanol | Nonwaxy | 10 | 8.11 | 8.60 | 9.09 | 0.47 | 0.69 | 1.26 | 0.22 |
| Ethanol | Waxy | 10 | 9.60 | 9.91 | 10.22 | 0.29 | 0.43 | 0.78 | 0.14 |
| Ethanol | Diff | | −1.85 | −1.31 | −0.77 | 0.43 | 0.57 | 0.85 | 0.26 |
| Variable | Method | Variances | DF | t Value | Pr > \|t\| | Significance | | | |
| Ethanol | Pooled | Equal | 18 | −5.11 | <.0001 | ** | | | |
| Ethanol | Satterthwaite | Unequal | 15 | −5.11 | 0.0001 | | | | |
| Variable | Method | Num DF | Den DF | F Value | Pr > F | Significance | | | |
| Ethanol | Folded F | 9 | 9 | 2.6 | 0.17 | | | | |

| | | | 48 hours data at 36% | | | | | |
|---|---|---|---|---|---|---|---|---|
| Variable | Line | N | Lower CL Mean | Mean | Upper CL Mean | Lower CL Std Dev | Std Dev | Upper CL Std Dev | Std Err |
| Ethanol | Nonwaxy | 10 | 8.15 | 8.30 | 8.46 | 0.15 | 0.21 | 0.39 | 0.07 |
| Ethanol | Waxy | 10 | 9.53 | 9.92 | 10.32 | 0.38 | 0.55 | 1.00 | 0.17 |
| Ethanol | Diff | | −2.01 | −1.62 | −1.23 | 0.31 | 0.42 | 0.62 | 0.19 |
| Variable | Method | Variances | DF | t Value | Pr > \|t\| | Significance | | | |
| Ethanol | Pooled | Equal | 18 | −8.7 | <.0001 | | | | |
| Ethanol | Satterthwaite | Unequal | 11.7 | −8.7 | <.0001 | ** | | | |
| Variable | Method | Num DF | Den DF | F Value | Pr > F | Significance | | | |
| Ethanol | Folded F | 9 | 9 | 6.57 | 0.0098 | ** | | | |

| | | | 72 hours data at 30% | | | | | |
|---|---|---|---|---|---|---|---|---|
| Variable | Line | N | Lower CL Mean | Mean | Upper CL Mean | Lower CL Std Dev | Std Dev | Upper CL Std Dev | Std Err |
| Ethanol | Nonwaxy | 10 | 9.67 | 10.20 | 10.74 | 0.51 | 0.74 | 1.36 | 0.24 |
| Ethanol | Waxy | 10 | 11.96 | 12.17 | 12.39 | 0.21 | 0.30 | 0.56 | 0.10 |
| Ethanol | Diff | | −2.50 | −1.97 | −1.44 | 0.43 | 0.57 | 0.84 | 0.25 |

-continued

| 72 hours data at 30% | | | | | | |
|---|---|---|---|---|---|---|
| Variable | Method | Variances | DF | t Value | Pr > \|t\| | Significance |
| Ethanol | Pooled | Equal | 18 | −7.76 | <.0001 | |
| Ethanol | Satterthwaite | Unequal | 11.9 | −7.76 | <.0001 | ** |

| Variable | Method | Num DF | Den DF | F Value | Pr > F | Significance |
|---|---|---|---|---|---|---|
| Ethanol | Folded F | 9 | 9 | 5.97 | 0.014 | * |

| 72 hours data at 36% | | | | | | | | | |
|---|---|---|---|---|---|---|---|---|---|
| Variable | Line | N | Lower CL Mean | Mean | Upper CL Mean | Lower CL Std Dev | Std Dev | Upper CL Std Dev | Std Err |
| Ethanol | Nonwaxy | 10 | 10.02 | 10.36 | 10.70 | 0.32 | 0.47 | 0.86 | 0.15 |
| Ethanol | Waxy | 9 | 11.81 | 12.28 | 12.76 | 0.42 | 0.62 | 1.19 | 0.21 |
| Ethanol | Diff | | −2.45 | −1.92 | −1.39 | 0.41 | 0.55 | 0.82 | 0.25 |

| Variable | Method | Variances | DF | t Value | Pr > \|t\| | Significance |
|---|---|---|---|---|---|---|
| Ethanol | Pooled | Equal | 17 | −7.67 | <.0001 | ** |
| Ethanol | Satterthwaite | Unequal | 14.9 | −7.56 | <.0001 | |

| Variable | Method | Num DF | Den DF | F Value | Pr > F | Significance |
|---|---|---|---|---|---|---|
| Ethanol | Folded F | 8 | 9 | 1.74 | 0.43 | |

The types of NIL inbreds (waxy and non-waxy) were paired with two solids levels (30% and 36%) in a factorial design. Results from the factorial design examining the impact on fermentation in terms of ethanol yield support the hypothesis that the waxy NIL has a faster rate of ethanol accumulation and total ethanol yield in both solids levels. There was strong evidence of significant increased ethanol yield of the waxy NIL by time interaction with the exception of 24 hours at 30% solids. This may be due to variation inherent with fermentation process.

| Randomization Schedule | | | | |
|---|---|---|---|---|
| Solids | Variety | Order | Reps | Time Point |
| 36 | Control | 1 | 3 | 24, 48, 72 |
| 36 | Non-Waxy | 2 | 3 | 24, 48, 72 |
| 36 | Non-Waxy | 3 | 3 | 24, 48, 72 |
| 36 | Waxy | 4 | 3 | 24, 48, 72 |
| 36 | Non-Waxy | 5 | 3 | 24, 48, 72 |
| 36 | Waxy | 6 | 3 | 24, 48, 72 |
| 36 | Non-Waxy | 7 | 3 | 24, 48, 72 |
| 36 | Waxy | 8 | 3 | 24, 48, 72 |
| 36 | Waxy | 9 | 3 | 24, 48, 72 |
| 36 | Control | 10 | 3 | 24, 48, 72 |
| 36 | Non-Waxy | 11 | 3 | 24, 48, 72 |
| 36 | Waxy | 12 | 3 | 24, 48, 72 |
| 36 | Non-Waxy | 13 | 3 | 24, 48, 72 |
| 36 | Non-Waxy | 14 | 3 | 24, 48, 72 |
| 36 | Waxy | 15 | 3 | 24, 48, 72 |
| 36 | Non-Waxy | 16 | 3 | 24, 48, 72 |
| 36 | Waxy | 17 | 3 | 24, 48, 72 |
| 36 | Waxy | 18 | 3 | 24, 48, 72 |
| 36 | Control | 19 | 3 | 24, 48, 72 |
| 36 | Non-Waxy | 20 | 3 | 24, 48, 72 |
| 36 | Waxy | 21 | 3 | 24, 48, 72 |
| 36 | Non-Waxy | 22 | 3 | 24, 48, 72 |
| 36 | Waxy | 23 | 3 | 24, 48, 72 |
| 30 | Waxy | 1 | 3 | 24, 48, 72 |
| 30 | Non-Waxy | 2 | 3 | 24, 48, 72 |
| 30 | Non-Waxy | 3 | 3 | 24, 48, 72 |
| 30 | Non-Waxy | 4 | 3 | 24, 48, 72 |
| 30 | Control | 5 | 3 | 24, 48, 72 |
| 30 | Waxy | 6 | 3 | 24, 48, 72 |
| 30 | Non-Waxy | 7 | 3 | 24, 48, 72 |
| 30 | Non-Waxy | 8 | 3 | 24, 48, 72 |
| 30 | Non-Waxy | 9 | 3 | 24, 48, 72 |
| 30 | Non-Waxy | 10 | 3 | 24, 48, 72 |
| 30 | Waxy | 11 | 3 | 24, 48, 72 |
| 30 | Waxy | 12 | 3 | 24, 48, 72 |
| 30 | Non-Waxy | 13 | 3 | 24, 48, 72 |
| 30 | Control | 14 | 3 | 24, 48, 72 |
| 30 | Waxy | 15 | 3 | 24, 48, 72 |
| 30 | Waxy | 16 | 3 | 24, 48, 72 |
| 30 | Waxy | 17 | 3 | 24, 48, 72 |
| 30 | Waxy | 18 | 3 | 24, 48, 72 |
| 30 | Non-Waxy | 19 | 3 | 24, 48, 72 |
| 30 | Non-Waxy | 20 | 3 | 24, 48, 72 |
| 30 | Waxy | 21 | 3 | 24, 48, 72 |
| 30 | Waxy | 22 | 3 | 24, 48, 72 |
| 30 | Control | 23 | 3 | 24, 48, 72 |

Experiment 3

Headspace Analysis of a Fermented Sample

Research Objective: Determine if Headspace Gas Chromatography is a Viable Option for the Ethanol HTS Platform.
Research Hypothesis:
Headspace gas chromatography coupled with flame ionization detection has been identified in the literature as a common method used to determine blood alcohol content.

This method of ethanol detection was applied to an alcoholic fermentation of *maize* in order to determine if the method was applicable for a high throughput screening platform. Included in the analysis were an ethanol sample, the analyte of interest, and an isopropanol sample, the intended internal standard for the proposed HTS method. The 2 alcohols were analyzed in order to determine if these could be resolved in a chromatogram.

Technical Approach: An Hewlett-Packard HP6890GC system with a Hewlett-Packard HP7694 headspace autosampler and an FID was used to analyze 3 sample materials. The 3 sample materials were: A) a 15% aqueous ethanol standard, B) a 10% aqueous isopropanol standard and C) a fermented *maize* mash sample.

Work Plan: Alcohol standards were created and dispensed in 20 ml headspace vials. The fermented *maize* mash was also placed in the 20 ml headspace vial. The samples were then analyzed following the same headspace and gas chromatography parameters.

Materials and Methods

Samples of fermented *maize*, a 15% aqueous ethanol standard and 10% isopropyl alcohol standard were prepared and placed in 20 ml headspace vials. The samples were then analyzed on the Hewlett-Packard headspace gas chromatograph with flame ionization detection. The column used in the GC was a DB1, (30 m×0.25 mm id, 0.25 μm film). The oven temperature was ramped from 55° to 100° C.

Results

The chromatogram of 15% ethanol standard shows good peak shape and a retention time of 2.01 minutes. There are no other peaks recorded on the chromatogram. The chromatogram of the fermented *maize* shows the ethanol peak at the same retention time as the standard, with a similar peak shape. There are a few minor peaks detected in the chromatogram, the largest of which is ≈0.25% of the height of the ethanol peak. The chromatogram of the 10% isopropanol standard shows a peak with a retention time of 3.26 minutes. The shape of the isopropanol peak is also good. The 3 sample chromatograms 15% Ethanol Standard, Fermented *Maize* and 10% Isopropanol Standard Discussion The use of headspace GC coupled with FID resulted in chromatograms that are very similar to those found in the literature. The analytical technique meets the requirements for the ethanol HTS platform. The resulting peak retention times and peak shapes of the ethanol and isopropanol samples indicate that resolving the 2 compounds will not be a problem.

Experiment 4

Investigation of NPA Volume and GC Method for High Throughput Fermentation Screening Research Objective Research Hypothesis: Corn Ethanol Platform has developed a high throughput screening assay to measure the rate of ethanol accumulation and total ethanol yield using gas chromatography (GC) analysis. The current process uses 1% 1-propanol (NPA) as the internal standard and a single rinse method between the injections. The objectives of this study are to determine the volume at which the NPA should be added to the ferments to reduce measurement errors and determine which method (single or dual rinse) observes a reduction in errors between the front and back injectors.

Technical Approach: 144 fermentations will take place in 20 mL headspace vials. The 144 fermentations are divided into 4 treatments with 12 reps per time point. The time points are 24, 48, and 72 hours. The 4 treatments are: 1) Dual 1%; 2) Dual 2.5%; 3) Single 1%; and 4) Single 2.5%. Table below summarizes the treatment groups.

TABLE

Sample Matrix of Investigation of NPA Volume and GC Method for High Throughput Fermentation Screening

| GC Method | NPA Volume | Reps | Time Points |
|---|---|---|---|
| 1) Dual Rinse | 1% NPA | 36 (12 per time point) | 24, 48, 72 hours |
| 2) Single Rinse | 2.5% NPA | 36 (12 per time point) | 24, 48, 72 hours |
| 3) Dual Rinse | 2.5% NPA | 36 (12 per time point) | 24, 48, 72 hours |
| 4) Single Rinse | 1% NPA | 36 (12 per time point) | 24, 48, 72 hours |

Work Plan: The samples will be fermented for 72 hours in the growth room at 30C. At 24, 48, and 72 hours, samples will be analyzed for ethanol analysis via GC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Genencor ® Spezyme Xtra | Ethanol Tech ® AYF1177 Nutrient |
| Distilled water | Tetracycline |
| Shaker | Oven |
| 20 mL headspace vials and caps | Growth Chamber |
| Analytical Balance | Powder handling system |
| Liquid handling system | Liquid chromatography |

Moisture was measured on the corn flour using the Perten DA NIR7200.

Use the "Dry-Grind Ethanol Calculator" and the measured moisture determines the appropriate amounts of corn flour, water, and alpha amylase to achieve 30% dry solids for liquefaction and place into seventy two (72) 20 mL headspace vials.

Liquefactions were carried out in an oven at 85° C. for 90 minutes. During liquefaction, shake the sample three times; approximately every 20 minutes during the process.

After the liquefaction, samples were cooled to room temperature.

Use the "Dry-Grind Ethanol Calculator" to determine the appropriate amounts of glucoamylase, nutrient, antimicrobial, and yeast based on 30% liquefaction dry solids to add into each sample.

After addition of fermentation components, shake each vial very well, and then set them to ferment at 30° C. in the growth chamber for 72 hours. A small hole should be punctured in each cap for ventilation during fermentation.

Samples are taken at 24, 48, and 72 hours for ethanol analysis via GC. Refer to Table below for analysis.

TABLE

Sample Matrix of Investigation of NPA Volume and GC Method for High Throughput Fermentation Screening

| GC Method | NPA Volume | Reps | Time Points |
|---|---|---|---|
| 1) Dual Rinse | 1% NPA | 36 (12 per time point) | 24, 48, 72 hours |
| 2) Single Rinse | 2.5% NPA | 36 (12 per time point) | 24, 48, 72 hours |
| 3) Dual Rinse | 1% NPA | 36 (12 per time point) | 24, 48, 72 hours |
| 4) Single Rinse | 2.5% NPA | 36 (12 per time point) | 24, 48, 72 hours |

Results and Discussion

Ethanol data at 24 hours:

|  | Dual 2.5% | Dual 1% | Single 2.5% | Single 1% |
|---|---|---|---|---|
| Mean | 6.39 | 6.34 | 5.48 | 5.37 |
| St. Dev | 0.37 | 0.33 | 0.82 | 0.61 |
| % RSD | 5.77 | 5.17 | 14.96 | 11.37 |
| Range | 1.16 | 1.19 | 3.01 | 2.06 |
| SEM | 0.11 | 0.09 | 0.24 | 0.18 |

Ethanol data at 48 hours:

|  | Dual 2.5% | Dual 1% | Single 2.5% | Single 1% |
|---|---|---|---|---|
| Mean | 7.84 | 7.64 | 6.63 | 6.33 |
| St. Dev | 0.62 | 0.73 | 0.69 | 0.51 |
| % RSD | 7.97 | 9.61 | 10.36 | 7.98 |
| Range | 1.98 | 2.35 | 2.07 | 1.56 |
| SEM | 0.21 | 0.23 | 0.21 | 0.15 |

Ethanol data at 72 hours:

|  | Dual 2.5% | Dual 1% | Single 2.5% | Single 1% |
|---|---|---|---|---|
| Mean | 9.87 | 9.50 | 7.96 | 8.08 |
| St. Dev | 0.49 | 0.65 | 0.94 | 0.78 |
| % RSD | 5.00 | 6.84 | 11.79 | 9.60 |
| Range | 1.44 | 2.36 | 2.67 | 2.49 |
| SEM | 0.14 | 0.19 | 0.27 | 0.22 |

Representative sample of surves are in shown in FIG. 4a-h.

Experiment 6

Confirmation and Selection of Fermentation Components

Research Objective

Research Hypothesis: One commercial available products screened have a measurable effect on the rate of ethanol accumulation or total ethanol yield when compared to our fermentation components. The leading components are Genencor's Spezyme Xtra alpha-amylase (commercial), Sigma's *A. Niger* glucoamylase (our benchmark), and Ethanol Tech's SLY yeast (benchmark). The nutrient and antibiotic components are still in question due to another competing component and sampling errors, respectively. The objective of this study is to ferment the leading and questionable components for confirmation of selection of fermentation components.

Technical Approach: Nine (9) fermentations will take place in 50 ml conical tubes. The 9 fermentations will be divided into 3 treatment groups with 3 reps per treatment. Table below summarizes the treatment

TABLE

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | *A. Niger* GA | *A. Niger* GA | *A. Niger* GA |
| Nutrient | Urea | AYF1177 | AYF1177 |
| Antibiotic | Tetracycline | Tetracycline | Lactoside |
| Yeast | SLY yeast | SLY yeast | SLY yeast |

Work Plan: The samples will be fermented for 72 hours in the growth room at 30C. At 24, 48, and 72 hours, each sample will be sub-sampled and prepared for ethanol analysis via liquid chromatography.

Materials and Methods

| | |
|---|---|
| Yellow dent corn | Perten 3600 Disc Mill |
| Perten DA7200 | Urea 1 g/2 ml Stock |
| VWR incubator | Sigma *A. niger* Glucoamylase |
| 50 ml conical tubes | Analytical balance |
| Tetracycline (10 mg/ml in 50% EtOH stock solution). | Ethanol Tech AYF 1177 |
| Genencor Spezyme Xtra | Ethanol Tech SLY Yeast |
| Ethanol Tech Lactoside | Growth chamber |

Grind yellow dent corn using Perten 3600 Disc Mill, on setting 0.

Moisture is measured on the flour using Perten DA7200.

Use the "Enzyme Confirmation Calculator" and the measured moisture to determine the appropriate amounts of yellow dent corn flour, water, and alpha amylase (Genencor's Spezyme Xtra) to achieve 30% dry solids and place into nine (9) 50 ml conical tubes for liquefaction.

Liquefactions are carried out in an oven at 85° C. for 90 minutes. During liquefaction, shake or vortex each tube every 20 minutes.

After the liquefaction, cool samples down to room temperature, and then, the samples were divided according to their treatment groups: Treatment 1 (3 samples), Treatment 2 (3 samples), and Treatment 3 (3 samples). Refer to Table 1.

TABLE 1

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | *A. Niger* GA | *A. Niger* GA | *A. Niger* GA |
| Nutrient | Urea | AYF1177 | AYF1177 |
| Antibiotic | Tetracycline | Tetracycline | Lactoside |
| Yeast | SLY yeast | SLY yeast | SLY yeast |

Use the "Enzyme Confirmation Calculator" to determine the appropriate amounts of glucoamylase, nutrient, antibiotic, and yeast to add to each sample.

After following each treatment design, mix the tubes very well, and then set them to ferment at 30° C. for 72 hours. A small hole should be punctured in each cap for ventilation during fermentation.

Samples are taken at 24, 48, and 72 hours for ethanol analysis via liquid chromatography.

Results and Discussion

TABLE 1

Sample Matrix for Fermentation of Leading Commerical Products and Questionable Components

|  | Treatment 1 | Treatment 2 | Treatment 3 |
|---|---|---|---|
| Alpha-amylase | Spezyme Xtra | Spezyme Xtra | Spezyme Xtra |
| Glucoamylase | *A. Niger* GA | *A. Niger* GA | *A. Niger* GA |
| Nutrient | Urea | AYF1177 | AYF1177 |
| Antibiotic | Tetracycline | Tetracycline | Lactoside |
| Yeast | SLY yeast | SLY yeast | SLY yeast |

Ethanol Data:

| At 24 hours: | | | At 48 hours: | | | At 72 hours: | | |
|---|---|---|---|---|---|---|---|---|
|  | Rep | ETOH % |  | Rep | ETOH % |  | Rep | ETOH % |
| Treatment 1 | 1 | 4.57 | Treatment 1 | 1 | 6.99 | Treatment 1 | 1 | 9.23 |
|  | 2 | 4.66 |  | 2 | 7.3 |  | 2 | 9.62 |
|  | 3 | 4.65 |  | 3 | 7.29 |  | 3 | 10.11 |
| Treatment 2 | 1 | 5.88 | Treatment 2 | 1 | 9.39 | Treatment 2 | 1 | NA |
|  | 2 | 8.02 |  | 2 | 6.97 |  | 2 | NA |
|  | 3 | 8.72 |  | 3 | 7.36 |  | 3 | NA |
| Treatment 3 | 1 | 4.74 | Treatment 3 | 1 | 7.62 | Treatment 3 | 1 | 10.05 |
|  | 2 | 4.81 |  | 2 | 7.7 |  | 2 | 10.37 |
|  | 3 | 4.69 |  | 3 | 7.23 |  | 3 | 9.68 |

Statistical analysis at 24 time point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 2.00 | 16.30 | 8.15 | 11.14 | 0.01 |
| Error | 6.00 | 4.39 | 0.73 | | |
| Corrected Total | 8.00 | 20.70 | | | |

| Source | DF | Type 1 SS | Mean Square | F Value | Pr > F |
|---|---|---|---|---|---|
| treatment | 2.00 | 16.30 | 8.15 | 11.14 | 0.01 |

| Source | DF | Type 3 SS | Mean Square | F Value | Pr > F |
|---|---|---|---|---|---|
| treatment | 2.00 | 16.30 | 8.15 | 11.14 | 0.01 |

| t Grouping | Mean | N | Treatment |
|---|---|---|---|
| A | 7.54 | 3.00 | 2 |
| B | 4.75 | 3.00 | 3 |
| B | 4.63 | 3.00 | 1 |

Statistical analysis at 48 hour time point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 2.00 | 0.77 | 0.38 | 0.64 | 0.56 |
| Error | 6.00 | 3.57 | 0.59 | | |
| Corrected Total | 8.00 | 4.33 | | | |

| Source | DF | Type 1 SS | Mean Square | F Value | Pr > F |
|---|---|---|---|---|---|
| treatment | 2.00 | 0.77 | 0.38 | 0.64 | 0.56 |

| Source | DF | Type 3 SS | Mean Square | F Value | Pr > F |
|---|---|---|---|---|---|
| treatment | 2.00 | 0.77 | 0.38 | 0.64 | 0.56 |

| t Grouping | Mean | N | Treatment |
|---|---|---|---|
| A | 7.91 | 3.00 | 2 |
| A | 7.52 | 3.00 | 3 |
| A | 7.19 | 3.00 | 1 |

Statistical analysis at 72 hour time point:

| Treatment | Treatment Code |
|---|---|
| Urea and Tetracycline | 1 |
| AYF1177 and Tetracycline | 2 |
| AYF1177 and Lactoside | 3 |

| Source | DF | Sum of Squares | Mean Square | F Value | Pr > F |
|---|---|---|---|---|---|
| Model | 1.00 | 0.22 | 0.22 | 1.38 | 0.31 |
| Error | 4.00 | 0.63 | 0.16 | | |
| Corrected Total | 5.00 | 0.84 | | | |

| Source | DF | Type 1 SS | Mean Square | F Value | Pr > F |
|---|---|---|---|---|---|
| treatment | 1.00 | 0.22 | 0.22 | 1.38 | 0.31 |

| Source | DF | Type 3 SS | Mean Square | F Value | Pr > F |
|---|---|---|---|---|---|
| treatment | 1.00 | 0.22 | 0.22 | 1.38 | 0.31 |

| t Grouping | Mean | N | Treatment |
|---|---|---|---|
| A | 10.03 | 3.00 | 3 |
| A | 9.65 | 3.00 | 1 |

The nutrient/antibiotic combination of AYF1177/Tetracycline used in Treatment 2 was found to be significantly different from the Urea/Tetracycline and AYF1177/Lactoside treatment's mean ethanol yields at 24 hours. There were no significant differences observed at the 48 and 72 hour time points. The 72 hour fermentation data for Treatment 2 is unavailable. The substitution of AYF1177 for Urea in our benchmark resulted in a significant increase in mean ethanol yields in 24 and 48 hour ferments. As a result of the observations made in these 2 studies, AYF1177 and Tetracycline are used as the nutrient and antibiotic in the high throughput fermentation platform.

Based on the standard deviation values and % RSD values of each treatment, the dual GC method appears to have less variation between the injectors than the single GC method.

The 2.5% NPA, with lower intercepts and consistent slopes in the calibration curves, appears to have a better correlation than the 1% NPA. Based on the results presented here, the dual GC method with 2.5% NPA was selected to optimize the high throughput fermentation platform.

Experiment 7

Method Optimization of Raw Starch Fermentation

Research Objective

Research Hypothesis: Corn Ethanol Platform has developed a high throughput screening assay to measure the rate of ethanol accumulation and total ethanol yield. In efforts to optimize the raw starch fermentation for calibration development, the objectives of this study are to: 1) determine the optimal doses of glucoamylase and yeast, 2) determine whether the pH of the ferments are within the desirable range, and 3) validate the pasteurization process used in the dry grind fermentation to inhibit yeast growth in the procedure.

Technical Approach: Three hundred sixty (360) fermentations will take place in 20 mL headspace vials. The 360 fermentations are divided into 25 unique enzyme dose combinations of glucoamylase and yeast at 33% solids. Each enzyme dose combination will be compared current dose rates of glucoamylase and yeast at 33% solids (100-100%=benchmark treatment). Each enzyme dose combination will have 4 reps per time point. The time points are 24, 48, and 72 hours. Table 1 summarizes the treatment groups.

An additional 5 treatments of the 100-100% benchmark dose combination will be prepared to investigate what effect the pasteurization process utilized on the high throughput fermentation screening platform has on the ethanol generation of the raw starch fermentation process. Three treatments of the 100-100% dose combination without pasteurization will be compared to 3 treatments which are pasteurized.

An additional 25 fermentations will take place in 20 mL headspace vials for pH measurements only. The measurements will occur before and after the addition of tetracycline, glucoamylase, and yeast and after 72 hours of fermentation. Each enzyme dose combination will have 1 rep.

TABLE

Sample Matrix for Method Optimization of Raw Starch Fermentation

| Sample | Time Point | Reps | Pasteurization |
|---|---|---|---|
| 1 | 75-75 | 24, 48, 72 | 12 (4/time point) | Yes |
| 2 | 75-88 | 24, 48, 72 | 12 (4/time point) | Yes |
| 3 | 75-100 | 24, 48, 72 | 12 (4/time point) | Yes |
| 4 | 75-112 | 24, 48, 72 | 12 (4/time point) | Yes |
| 5 | 75-125 | 24, 48, 72 | 12 (4/time point) | Yes |
| 6 | 88-75 | 24, 48, 72 | 12 (4/time point) | Yes |
| 7 | 88-88 | 24, 48, 72 | 12 (4/time point) | Yes |
| 8 | 88-100 | 24, 48, 72 | 12 (4/time point) | Yes |
| 9 | 88-112 | 24, 48, 72 | 12 (4/time point) | Yes |
| 10 | 88-125 | 24, 48, 72 | 12 (4/time point) | Yes |
| 11 | 100-75 | 24, 48, 72 | 12 (4/time point) | Yes |
| 12 | 100-88 | 24, 48, 72 | 12 (4/time point) | Yes |
| 13 | 100-100 | 24, 48, 72 | 12 (4/time point) | Yes |
| 14 | 100-100 | 24, 48, 72 | 12 (4/time point) | Yes |
| 15 | 100-100 | 24, 48, 72 | 12 (4/time point) | Yes |
| 16 | 100-100 | 24, 48, 72 | 12 (4/time point) | NO |
| 17 | 100-100 | 24, 48, 72 | 12 (4/time point) | NO |
| 18 | 100-100 | 24, 48, 72 | 12 (4/time point) | NO |
| 19 | 100-112 | 24, 48, 72 | 12 (4/time point) | Yes |
| 20 | 100-125 | 24, 48, 72 | 12 (4/time point) | Yes |
| 21 | 112-75 | 24, 48, 72 | 12 (4/time point) | Yes |
| 22 | 112-88 | 24, 48, 72 | 12 (4/time point) | Yes |
| 23 | 112-100 | 24, 48, 72 | 12 (4/time point) | Yes |
| 24 | 112-112 | 24, 48, 72 | 12 (4/time point) | Yes |
| 25 | 112-125 | 24, 48, 72 | 12 (4/time point) | Yes |
| 26 | 125-75 | 24, 48, 72 | 12 (4/time point) | Yes |
| 27 | 125-88 | 24, 48, 72 | 12 (4/time point) | Yes |
| 28 | 125-100 | 24, 48, 72 | 12 (4/time point) | Yes |
| 29 | 125-112 | 24, 48, 72 | 12 (4/time point) | Yes |
| 30 | 125-125 | 24, 48, 72 | 12 (4/time point) | Yes |
| | | TOTAL | 360 | |

Work Plan: The samples will randomized over 2 days of fermentation. Each sample will be fermented for 72 hours in the growth room at 30C. At 24, 48, and 72 hours, each sample will be sub-sampled and prepared for ethanol analysis via HPLC.

Materials and Methods

| | |
|---|---|
| Yellow dent corn | Perten DA NIR7200 |
| Sigma *A. Niger* Glucoamylase | Ethanol Tech ® Stabilized Liquid Yeast |
| Distilled water | Tetracycline 10 mg/ml in 50% EtOH |
| Fluid Management ® 5G High Speed Shaker | 0.9M Sulfuric Acid |
| 20 mL headspace vials and caps | Growth Chamber |
| Analytical Balance | SDSI 2300 Powder Dispensing System |
| Hamilton MicroLab ® 500 Liquid Handling System | Agilent 1200 series HPLC with RID & Quaternary Pump System |
| pH indicator strips | 22 Gauge Needles |

Measure the moisture of the corn flour using the Perten DA NIR7200.

Use the "Raw Starch Calculator" and the measured moisture to determine the appropriate amounts of corn flour, water, sulfuric acid, tetracycline, glucoamylase, and yeast to achieve 33% solids and place into three hundred sixty (360) 20 mL headspace vials.

Add the components in the following order: water, sulfuric acid, tetracycline, glucoamylase, and yeast.

Vortex the vials after the addition of water, and vortex the vials a second time after the addition of sulfuric acid. Refer to Table 1.

After the addition of tetracycline, glucoamylase, and yeast, use the high speed shaker to mix the fermentation components very well, and then set them to ferment at 30° C. in the growth chamber for 72 hours. A needle should be punctured in each cap for ventilation during fermentation.

Samples are taken at 24, 48, and 72 hours for ethanol analysis via HPLC.

Results and Discussion

Objective 1—GA & Yeast Doses Investigated

The data analysis of the glucoamylase and yeast dosage study was performed.

An analysis of variance was performed controlling for session, glucoamylase dose, yeast dose, and the interaction between glucoamylase and yeast. Separate analyses were performed for each time point.

At 24 hours, there was evidence of differences in ethanol concentration attributable to dose of glucoamylase (p=0.021), but there was not evidence of differences attributable to dose of yeast (p=0.840) or to an interaction effect (p=0.973). Least squares means were computed for each dose of glucoamylase, but there was not sufficient evidence to suggest that any experimental dose of glucoamylase resulted in higher ethanol concentrations than was observed with the baseline dose. See Table 1 at the end of the report.

At 48 hours, there was strong evidence of differences in ethanol concentration attributable to dose of glucoamylase (p<0.001), but there was not evidence of differences attributable to dose of yeast (p=0.748) or to an interaction effect (p=0.914). Least squares means were computed for each dose of glucoamylase. There was weak evidence to suggest that the 112.5% and 125% doses of glucoamylase resulted in higher ethanol concentration than did the 100% dose of glucoamylase. However, the relative magnitude of the increase in ethanol concentrations is less than 2% and likely is not of practical significance. See Table 1 at the end of the report.

At 72 hours, there was no evidence of differences in ethanol concentration attributable to dose of glucoamylase (p=0.419), dose of yeast (p=0.193) or to an interaction effect (p=0.360). Least squares means are presented in Table 1 at the end of this report.

Results from a factorial design examining the impact of manipulating the dose of glucoamylase and the dose of yeast do not support the hypothesis that the dose of yeast affects ethanol concentration, at least within the range of doses included in the study (75% -125% of baseline). There was weak evidence of an increased ethanol concentration with higher levels of glucoamylase at 48 hours only, but the magnitude of this effect is less than 2% in size and likely is not of practical significance.

TABLE

Least Squares Means for Ethanol Concentration by Time and Dose of GA

| Glucoamylase Dose | Ethanol Concentration at: | | |
| --- | --- | --- | --- |
| | 24 Hours | 48 Hours | 72 Hours |
| 75.0% | 8.85 | 14.36 | 17.27 |
| 87.5% | 9.35 | 14.83 | 17.48 |
| 100.0% | 9.71 | 14.83 | 17.68 |
| 112.5% | 9.53 | 15.08 | 17.79 |
| 125.0% | 9.82 | 15.09 | 17.00 |

Plots of this data can be generated. Plots of the least squares means for ethanol content vs. glucoamylase concentration, illustrating the differences observed between the glucoamylase treatments at the 24, 48 and 72 hour fermentation periods can be visualized.

Objective 2—pH Measurements

The raw starch fermentation method calls for the use of 0.9 M sulfuric acid at a rate of 0.0175 ml/g of dry flour to adjust the pH to 4.2 before fermentation begins. We found that gave us a pH of 4.9 before and after the addition of tetracycline, glucoamylase, and yeast. After 72 hours of fermentation, the pH dropped to 4.2. Table below summarizes the results of the pH measurements.

TABLE

Resulting pH values after addition of $H_2SO_4$, Yeast and after 72 hr Fermentation

| Sample | | pH Reading After $H_2SO_4$ Addition | pH Reading After Yeast Addition | pH Reading After 72 Hours Fermentation |
| --- | --- | --- | --- | --- |
| 1 | 75-75 | 4.6 | 4.9 | 4.2 |
| 2 | 75-88 | 4.6 | 4.9 | 4.2 |
| 3 | 75-100 | 4.9 | 4.9 | 4.2 |
| 4 | 75-112 | 4.6 | 4.9 | 4.2 |
| 5 | 75-125 | 4.9 | 4.9 | 4.2 |
| 6 | 88-75 | 4.9 | 4.9 | 4.2 |
| 7 | 88-88 | 4.6 | 4.9 | 4.2 |
| 8 | 88-100 | 4.6 | 4.9 | 4.2 |
| 9 | 88-112 | 4.9 | 4.9 | 4.2 |
| 10 | 88-125 | 4.6 | 4.9 | 4.2 |
| 11 | 100-75 | 4.9 | 4.9 | 4.2 |
| 12 | 100-88 | 4.9 | 4.9 | 4.2 |
| 13 | 100-100 | 4.9 | 4.9 | 4.2 |
| 14 | 100-112 | 4.9 | 4.9 | 4.2 |
| 15 | 100-125 | 4.9 | 4.9 | 4.2 |
| 16 | 112-75 | 5.2 | 5.2 | 4.4 |
| 17 | 112-88 | 5.2 | 5.2 | 4.4 |
| 18 | 112-100 | 5.2 | 5.2 | 4.4 |
| 19 | 112-112 | 5.2 | 4.9 | 4.2 |
| 20 | 112-125 | 5.2 | 4.9 | 4.2 |
| 21 | 125-75 | 4.9 | 4.9 | 4.4 |
| 22 | 125-88 | 4.9 | 4.9 | 4.4 |
| 23 | 125-100 | 4.9 | 4.9 | 4.2 |
| 24 | 125-112 | 4.9 | 4.9 | 4.2 |
| 25 | 125-125 | 4.9 | 4.9 | 4.2 |

Objective 3—Arresting Method

Significant differences were observed between the treatments that were pasteurized and the treatments that were not pasteurized. The untreated samples continued to increase in ethanol over time and are significantly greater than the dose combinations that were treated with 45 minute pasteurization, indicating that yeast growth has been arrested in the pasteurized samples. Table below summarizes the mean ethanol percent at each time period and the treatment significance between the pasteurized and untreated samples.

TABLE

Treatment Significance and Mean Ethanol Percent at Each Time Period

| | With Pasteurization | Without Pasteurization | P-Values |
| --- | --- | --- | --- |
| 24 Hours | 9.48 | 10.81 | 0.0003 |
| 48 Hours | 14.93 | 16.82 | <.0001 |
| 72 Hours | 17.63 | 18.91 | <.0001 |

Experiment 8

Seed Selection Based on Ethanol

The method of selecting seed for use in a monocot or dicot breeding and/or development program. This high throughput screen is very useful for selecting grass seeds with increased ethanol content for use in breeding or for commercial use of the seed. For example, grass seeds such as sorghum, wheat, oats, switch grass, or *maize* may be selected with this high throughput screen directly.

This screening method destroys the analyzed seed so there must be around 500-1000 seeds in total allow for screening with some seeds being retained for use as selected seeds for breeding. Alternatively, use of the NIR seed calibration, developed by the use of the screen to detect high ethanol content within *maize* seeds can be employed in a non-seed destruct method. This calibration allows even the very early breeding material (when there are few seeds) to be analyzed for ethanol content and then based on the analysis either selected for or discarded from use in further breeding.

A NIR calibration or results from the screen can be used to select inbred seeds or hybrid seeds for high, medium or low ethanol content. Either the calibration or the screen result will allow the breeder or hybrid developer to select inbreds for: breeding, development or use in hybrid combinations based on ethanol content. Additionally, the NIR calibration or screen results can be used to select hybrids which will produce high levels of ethanol content from the grain. Additionally, grain harvested from hybrid plants can be analyzed by either method to select hybrid seed which produces the highest level of ethanol from the grain. This selected material can be used in a breeding program that continually reassesses each generation for ethanol or it can be used intermittently within the breeding process or just as a final selection tool.

Because NIR calibrations and screen results are possible on subsets of seeds components, the starch itself or just a portion of the seed, for example an embryo less seed, very small quantities of breeding seeds can be analyzed according to the present invention for ethanol content. If embryo less seeds are used then the embryos of these seeds can be employed in embryo rescue techniques to still produce a plant. Thus when the invention employs a step of embryo removal from the seed both the NIR ethanol calibration and the screen are non seed destruct processes. Non seed destruct is important when seeds are limited in number such as seeds from a segregating breeding population, doubled haploid seeds or seeds from lines that are not fully fixed.

Additionally, because the screen allows for testing of different fermentation cocktails the present invention allows different types of seed to be selected for use in hybrids that are processed through ethanol plants that employ different fermentation cocktails. This screen also allows hybrid blends to be selected and developed so that hybrid seed with produce grain that provides the highest ethanol content can be produced in regardless of which fermentation cocktails ethanol processors are employing. Hybrid blends are very useful in an area where there may be more than one ethanol processing plant and these different plants are using different enzymes, or different levels of enzymes during the ethanol production.

Definitions

Definitions for calculations

Dry Grind Calculator

Liquefaction
  Given variables (as an example):
    ul's of benchmark amylase/dry gram corn flour=0.29
    Commodity corn % moisture=5% (measured by Perten Diode Array 7200 instrument)
    Wet commodity corn to weigh into each vial (g wet weight)=3 g
    Target % dry solids liquefaction=30%

Dry gram corn flour for liquefaction (g dry weight):

Wet commodity corn (g wet weight)−((Wet commodity corn (g wet weight)×(Commodity Corn % moisture/100))

$3-(3\times(5/100))=2.85$ g

Total ul's of benchmark amylase to add to each vial at 1/25 dilution:

Dry gram corn flour for liquefaction (g dry weight)× (ul's of benchmark amylase/dry gram corn flour)×25

$2.85\times 0.29\times 25=20.66$ ul

Water in corn (g weight):

Wet commodity corn (g wet weight)−Dry gram corn flour for liquefaction (g dry weight)

$3-2.85=0.15$ g

Total water volume in each vial (ml):

(Dry gram corn flour for liquefaction (g dry weight)/ 30%)−Dry gram corn flour for liquefaction (g dry weight)−Water in corn (g weight)

$(2.85/30\%)-2.85-0.15=6.50$ ml

Water to add to each vial (ml):

Total water volume in each vial (ml)−((Total ul's of benchmark to add to each vial at 1/25 dilution/ 1000)+Water in corn (g weight))

$6.50-((20.66/1000)+0.15)=6.33$ ml

Total mass of liquefact (g):

Wet commodity corn (g wet weight)+Total water volume in each vial (ml)

$3+6.50=9.50$ g

Fermentation
  Given variables (as an example):
    Tetracycline 10 mg/ml use rate per gram flour (ml/g flour)=0.005 AYF1177 use rate per gram flour (ml/g flour)=0.00015
    *A. niger* glucoamylase use rate per gram flour (ul/g flour)=0.963
    SLY yeast use rate per gram flour (ul/g slurry)=10
  Desired mass of corn flour in ferment (g dry weight):

Dry gram corn flour for liquefaction (g dry weight)

2.85 g

Mass of liquefact needed for ferment (g):

((Wet commodity corn (g wet weight)+Total water volume in each vial (ml))/Dry gram corn flour for liquefaction (g dry weight))×Desired mass of corn flour in ferment (g dry weight)

$((3+6.50)/2.85)\times 2.85=9.50$ g

Tetracycline 10 mg/ml in 50% EtOH stock solution to add to each vial (ml):

Desired mass of corn flour in ferment (g dry weight)× Tetracycline 10 mg/ml use rate (ml/g flour)

$2.85\times 0.005=0.01425$ ml

AYF1177 at 1/20 dilution to add to each vial (ml):

Desired mass of corn flour in ferment (g dry weight)× AYF1177 use rate (ml/g flour)×20

$2.85\times 0.00015\times 20=0.00855$ ml

A. niger glucoamylase at 1/20 dilution to add to each vial (ml):

(Desired mass of corn flour in ferment (g dry weight)×
A. niger glucoamylase use rate (ul/g flour)×20)/
1000

(2.85×0.963×20)/1000=0.0549 ml

SLY yeast at 1/10 dilution to add to each vial (ml):

(Total mass of liquefact (g)×SLY yeast use rate (ul/g flour)×10)/1000

(9.50×10×10)/1000=0.95 ml

Sum volume of liquids to be added to ferment (ml):

Tetracycline 10 mg/ml in 50% EtOH stock solution (ml)+AYF1177 at 1/20 dilution (ml)+A. niger glucoamylase at 1/20 dilution (ml)+SLY yeast at 1/6 dilution (ml)

0.01425+0.00855+0.0549+0.95=1.03 ml

% Dry solids for fermentation:

Desired mass of corn flour in ferment (g dry weight)/
(Mass of liquefact needed for ferment (g)+Sum volume of liquids to be added to ferment (ml))

(2.85/(9.50+1.03))×100=27.07%

Raw Starch Calculator

Liquefaction
  NA
Fermentation
  Given variables (as an example):
    Corn flour moisture content %=5% (measured by Perten Diode Array 7200 instrument)
    Wet commodity corn to weigh into each vial (g wet weight)=3 g
    Target % dry solids=33%
    0.9 M H2SO4 use rate per gram flour (ml/g flour)= 0.0175
    Tetracycline 10 mg/ml use rate per gram flour (ml/g flour)=0.005
    A. niger glucoamylase use rate per gram flour (ml/g flour)=0.00521
    SLY yeast use rate per gram flour (ml/g flour)=0.03
  Dry gram corn flour for fermentation reaction (g dry weight):

Wet commodity corn (g wet weight)−((Wet commodity corn (g wet weight)×(Corn flour moisture content %/100))

3−(3×(5/100))=2.85 g

Water in corn (g weight):

Wet commodity corn (g wet weight)−Dry gram corn flour for fermentation reaction (g dry weight)

3−2.85=0.15 g

Total water volume in each vial (ml):

(Dry gram corn flour for fermentation reaction (g dry weight)/33%)−Dry gram corn flour for fermentation reaction (g dry weight)−Water in corn (g weight)

(2.85/33%)−2.85−0.15=5.64 ml

Water to add to each vial (ml):

Total water volume in each vial (ml)−(0.9 M H2SO4 (ml)+Tetracycline at 10 mg/ml (ml)+A. niger glucoamylase at 1/10 dilution (ml)+SLY yeast at 1/10 dilution (ml))

5.64−(0.05+0.0143+0.148+0.855)=4.57 ml 0.9 M H2SO4 to add to each vial (ml):

Dry gram corn flour for fermentation reaction (g dry weight)×0.9 M H2SO4 use rate (ml/g flour)

2.85×0.0175=0.05 ml

Tetracycline 10 mg/ml in 50% EtOH stock solution to add to each vial (ml):

Dry gram corn flour for fermentation reaction (g dry weight)×Tetracycline use rate (ml/g flour)

2.85×0.005=0.0143 ml

A. niger glucoamylase at 1/10 dilution to add to each vial (ml):

Dry gram corn flour for fermentation reaction (g dry weight)×A. niger glucoamylase use rate (ml/g flour)×10

2.85×0.00521×10=0.148 ml

SLY yeast at 1/10 dilution to add to each vial (ml):

Dry gram corn flour for fermentation reaction (g dry weight)×SLY yeast use rate (ml/g flour)×10

2.85×0.03×10=0.855 ml

Fermentation reaction sum (ml):

Tetracycline 10 mg/ml (ml)+A. niger glucoamylase 1/10 dilution (ml)+SLY yeast 1/10 dilution (ml)

0.0143+0.148+0.855=1.02 ml

Experiment

The High Throughput Screening Platform is made up of a number of processes. These include a. grinding, b. drying corn flour, c. weighing flour, d. water, nutrient, antibiotic and enzyme addition, e. liquefaction, add fermentation cocktail, f. fermentation, stop fermentation, g. pasteurization, and h. headspace analysis via gas chromatography. The calculator for different components is based on g of dry flour and all liquefactions and fermentations are assembled accordingly. Therefore it is imperative that the percent moisture of corn flour be determined.

i) Grinding—standard disc mill grinder is used.
j) Drying corn flour—the corn flour is driven to a terminal moisture level in a desiccating cabinet. The RH of the moisture cabinet may be from 5 to 20%, with a temperature range of 20 to 35° C.
k) Weighing Flour—Corn flour is weighed in a moisture-controlled glove box using an automated flour-dispensing unit. The RH of the glove box is maintained from 0-20%.
l) Addition of water, nutrient, antibiotic and enzymes—Each of the components listed are dispensed using computer controlled, repeating, dispensing units. Dispensing ranges are from 10 ul to 10 ml
m) Liquefaction—performed at a temperature range of about 75 to 95° C. for about 1 to 2 hours.
n) Fermentation—performed in 30±5° C. growth chambers. Ferments are allowed to grow for 24, 48 and 72 hours.

o) Pasteurization—to stop the fermentation process, the samples are pasteurized in a convected oven set at 80-90° C. for a period of 40-60 minutes.

p) Headspace analysis via gas chromatography—to analyze the samples ethanol content headspace GC analysis is utilized. The sample is incubated at 45±5° C. for 1.5 to 1.8 minutes. A headspace sample is then removed with a 46±5° C. heated syringe. The syringe then is injected into a 250±5° C. injection port, with a split flow of 25:1. The sample components are separated on an Agilent DB-ALC1 column at an isothermic oven temperature of 75±5° C. with a column flow of 7.5±0.5 ml/min.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A high throughput method for converting starch-containing plant material to one or more fermentation products comprising:
   providing a plurality of samples comprising starch-containing plant material;
   drying said samples to achieve a specific moisture level;
   liquefying each sample by heating the sample in a convected oven to obtain a liquefact,
   fermenting the liquefact of each sample in a small volume container under conditions sufficient for obtaining one or more fermentation products;
   pasteurizing said samples under conditions sufficient to terminate fermentation;
   wherein one or more fermentation products is produced.

2. The method of claim 1, wherein said samples are dried to a terminal moisture level.

3. The method of claim 1, wherein said fermentation product is ethanol.

4. The method of claim 1, wherein the liquefying step comprises addition of one or more starch-degrading enzymes.

5. The method of claim 1, wherein the starch-containing plant material is processed prior to the step of drying said samples.

6. The method of claim 1, wherein said method is modeled for length of time or temperature, or both, of liquefaction.

7. The method of claim 1, wherein said method is modeled for the source of starch-containing plant material.

8. The method of claim 1, wherein said method is modeled for the pH of the liquefying step.

9. The method of claim 1, wherein said method further comprises a saccharification step.

10. The method of claim 1, further comprising a step of weighing an amount of each of the dried samples for the liquefying step, wherein said weighing is performed in a climate-controlled glove box set at a relative humidity sufficient to maintain the specific moisture level of said samples.

11. The method of claim 3, wherein the ethanol is evaluated using headspace gas chromatography.

12. The method of claim 4, wherein the one or more starch-degrading enzymes comprises alpha-amylase.

13. The method of claim 4, wherein said method is modeled for the source of starch-degrading enzyme, the type of starch-degrading enzyme, the specific combination of starch-degrading enzymes, or any combination thereof.

14. The method of claim 5, wherein the starch-containing plant material is processed by milling said plant material.

15. The method of claim 9, wherein said saccharification step is a simultaneous liquefaction and saccharification step.

16. The method of claim 9, wherein said saccharification step is a simultaneous saccharification and fermentation step.

* * * * *